US010918559B2

(12) United States Patent
Romo et al.

(10) Patent No.: US 10,918,559 B2
(45) Date of Patent: Feb. 16, 2021

(54) INTERFACE SYSTEM IN AN EXOSKELETON

(71) Applicant: OSSUR ICELAND EHF, Reykjavik (IS)

(72) Inventors: Harry Duane Romo, Foothill Ranch, CA (US); Patrick Kiruki, Foothill Ranch, CA (US); Helga Run Palsdottir, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 434 days.

(21) Appl. No.: 15/961,069

(22) Filed: Apr. 24, 2018

(65) Prior Publication Data

US 2018/0303699 A1    Oct. 25, 2018

Related U.S. Application Data

(60) Provisional application No. 62/590,844, filed on Nov. 27, 2017, provisional application No. 62/583,140, (Continued)

(51) Int. Cl.
*A61H 3/00* (2006.01)
*A61F 5/01* (2006.01)
*A61H 1/02* (2006.01)

(52) U.S. Cl.
CPC .............. *A61H 3/00* (2013.01); *A61F 5/013* (2013.01); *A61H 1/0274* (2013.01);
(Continued)

(58) Field of Classification Search
CPC .. A61H 3/00; A61H 1/0274; A61H 2201/165; A61H 2201/1621;
(Continued)

(56) References Cited

U.S. PATENT DOCUMENTS 3,358,678 A    12/1967 Kultsar
3,449,769 A    6/1969 Mizen
(Continued)

FOREIGN PATENT DOCUMENTS

DE    19940603 A1    4/2001
FR    2917323 A1    12/2008
(Continued)

OTHER PUBLICATIONS

International Search Report from PCT Application No. PCT/US2018/029012, dated Aug. 8, 2018.
(Continued)

*Primary Examiner* — Tarla R Patel
(74) *Attorney, Agent, or Firm* — Workman Nydegger

(57) ABSTRACT

An interface system in an exoskeleton includes a base support, a strap assembly, and posterior strut. The posterior strut has a vertical member defining a lower end connecting to the base support, and an upper end connecting to first and second transverse members extending in opposed directions from the vertical member. The first and second transverse members connect to the strap assembly. The interface system is adapted to receive and support an assistive device adapted to augment a user's performance and mitigate repetitive strain injuries.

18 Claims, 13 Drawing Sheets

Related U.S. Application Data filed on Nov. 8, 2017, provisional application No. 62/489,618, filed on Apr. 25, 2017.

(52) U.S. Cl.
CPC .............. *A61H 2003/007* (2013.01); *A61H 2201/0192* (2013.01); *A61H 2201/163* (2013.01); *A61H 2201/165* (2013.01); *A61H 2201/1614* (2013.01); *A61H 2201/1621* (2013.01); *A61H 2201/1623* (2013.01); *A61H 2201/1635* (2013.01); *A61H 2201/1638* (2013.01); *A61H 2201/1652* (2013.01)

(58) Field of Classification Search
CPC ...... A61H 2201/1638; A61H 2201/163; A61H 2003/007; A61H 2201/1652; A61H 2201/0192; A61H 2201/1623; A61H 2201/1635; A61H 2201/1614; A61F 5/013; A61F 5/026; A61F 5/028; A61F 5/05808; A61F 5/37; A61F 2007/0024; A61F 2007/0025; A61F 2007/0026; A61F 2007/0027
USPC ........................................................... 602/19
See application file for complete search history.

(56) References Cited

U.S. PATENT DOCUMENTS

| | | |
|---|---|---|
| 4,180,870 A | 1/1980 | Radulovic et al. |
| 4,298,149 A | 11/1981 | Gottschalk et al. |
| 4,669,451 A | 6/1987 | Blauth et al. |
| 4,836,195 A | 6/1989 | Berrehail |
| 4,896,660 A | 1/1990 | Scott |
| 5,282,460 A | 2/1994 | Boldt |
| 5,385,536 A | 1/1995 | Burkhead et al. |
| 5,407,420 A | 4/1995 | Bastyr et al. |
| 5,954,250 A | 9/1999 | Hall et al. |
| 6,113,562 A | 9/2000 | Bonutti et al. |
| 6,190,343 B1 | 2/2001 | Heinz et al. |
| 6,267,741 B1 | 7/2001 | Lerman |
| 6,301,526 B1 | 10/2001 | Kim et al. |
| 6,599,263 B1 | 7/2003 | Bonutti et al. |
| 6,685,662 B1 | 2/2004 | Curry et al. |
| 6,929,616 B2 | 8/2005 | Bonutti et al. |
| 7,025,737 B2 | 4/2006 | Modglin |
| 7,316,660 B1 | 1/2008 | Modglin |
| 7,410,338 B2 | 8/2008 | Schiele et al. |
| 7,413,554 B2 | 8/2008 | Kobayashi et al. |
| 7,549,970 B2 | 6/2009 | Tweardy |
| 7,862,524 B2 | 1/2011 | Carignan et al. |
| 7,947,004 B2 | 5/2011 | Kazerooni et al. |
| 7,955,285 B2 | 6/2011 | Bonutti et al. |
| 8,066,654 B2 | 11/2011 | Sandifer et al. |
| 8,152,699 B1 | 4/2012 | Ma et al. |
| 8,172,779 B2 | 5/2012 | Ingimundarson et al. |
| 8,273,043 B2 | 9/2012 | Bonutti et al. |
| 8,303,528 B2 | 11/2012 | Ingimundarson et al. |
| 8,308,670 B2 | 11/2012 | Sandifer et al. |
| 8,356,604 B2 * | 1/2013 | Tweardy .............. A61F 5/055 128/870 |
| 8,409,118 B2 | 4/2013 | Agrawal et al. |
| 8,425,436 B2 | 4/2013 | Sankai |
| 8,460,222 B2 | 6/2013 | Garrec |
| 8,556,840 B2 | 10/2013 | Burke et al. |
| 8,591,442 B2 | 11/2013 | Bonutti et al. |
| 8,641,782 B2 | 2/2014 | Kim et al. |
| 8,657,769 B2 | 2/2014 | Ingimundarson et al. |
| 8,758,284 B1 | 6/2014 | Kozersky |
| 8,795,215 B2 | 8/2014 | Rossi |
| 8,926,537 B2 | 1/2015 | Ingimundarson et al. |
| 8,968,222 B2 | 3/2015 | Kazerooni et al. |
| 8,992,452 B2 * | 3/2015 | Carter .................. A61F 5/028 602/19 |
| 9,144,528 B2 | 9/2015 | Agrawal et al. |
| 9,155,651 B2 | 10/2015 | Ochoa |
| 9,204,730 B2 | 12/2015 | Brown |
| 9,205,017 B2 | 12/2015 | Doyle |
| 9,220,625 B2 | 12/2015 | Ingimundarson et al. |
| 9,345,606 B2 | 5/2016 | Bonutti et al. |
| 9,358,173 B2 | 6/2016 | Fu et al. |
| 9,375,325 B2 | 6/2016 | Garrec et al. |
| 9,404,618 B2 | 8/2016 | Brown et al. |
| 9,414,953 B2 | 8/2016 | Ingimundarson et al. |
| 9,427,865 B2 | 8/2016 | Doyle |
| 9,504,596 B1 | 11/2016 | Kozersky |
| 9,522,077 B1 | 12/2016 | Johnson |
| 9,572,705 B2 | 2/2017 | Ingimundarson et al. |
| 9,597,219 B2 | 3/2017 | Ingimundarson et al. |
| 9,636,247 B2 | 5/2017 | Miller et al. |
| 9,889,554 B2 * | 2/2018 | Van Engelhoven ..... B65H 1/10 |
| 2003/0115954 A1 | 6/2003 | Zemlyakov et al. |
| 2003/0220594 A1 | 11/2003 | Halvorson et al. |
| 2007/0060445 A1 | 3/2007 | Reinkensmeyer et al. |
| 2007/0225620 A1 | 9/2007 | Carignan et al. |
| 2008/0262401 A1 | 10/2008 | Wagner et al. |
| 2010/0204804 A1 | 8/2010 | Garrec |
| 2010/0217163 A1 | 8/2010 | Sankai |
| 2010/0318010 A1 | 12/2010 | Sandifer et al. |
| 2011/0127390 A1 | 6/2011 | Brown |
| 2012/0010749 A1 | 1/2012 | Van Der Merwe et al. |
| 2012/0172769 A1 | 7/2012 | Garrec |
| 2012/0179075 A1 | 7/2012 | Perry et al. |
| 2012/0184880 A1 | 7/2012 | Doyle |
| 2014/0033391 A1 | 2/2014 | Doyle |
| 2014/0100501 A1 | 4/2014 | Burke et al. |
| 2014/0158839 A1 | 6/2014 | Doyle |
| 2014/0371646 A1 * | 12/2014 | Kozersky ................ A61F 5/028 602/19 |
| 2015/0048134 A1 | 2/2015 | Fawcett et al. |
| 2015/0076196 A1 | 3/2015 | Brown et al. |
| 2015/0217444 A1 | 8/2015 | Asada et al. |
| 2015/0316204 A1 | 11/2015 | Doyle |
| 2016/0081871 A1 | 3/2016 | Doyle |
| 2016/0206497 A1 | 7/2016 | Deshpande et al. |
| 2016/0250061 A1 | 9/2016 | Ingimundarson et al. |
| 2016/0339583 A1 | 11/2016 | Van Engelhoven et al. |
| 2017/0007435 A1 | 1/2017 | Klutts |
| 2017/0156911 A1 | 6/2017 | Ingimundarson et al. |
| 2017/0173783 A1 | 6/2017 | Angold et al. |
| 2017/0189220 A1 | 7/2017 | Ingimundarson et al. |

FOREIGN PATENT DOCUMENTS

| | | |
|---|---|---|
| JP | 2008220883 A | 9/2008 |
| KR | 20150003562 U | 10/2015 |
| WO | 9532842 A2 | 12/1995 |
| WO | 2008031023 A2 | 3/2008 |

OTHER PUBLICATIONS

Etherington et al., "Hyundai's Future Mobility Plans Include Wearable Robotic Assistants," Tech Cruch, Dec. 19, 2016, 10 Pages, https://techcrunch.com/2016/12/19/hyundais-future-mobility-plans-include-wearable-robotic-assistants/.

"Ford Pilots New Exoskeleton Technology to Help Lessen Chance of Worker Fatigue, Injury," Ford Media Center, Nov. 9, 2017, 2 Pages, https://media.ford.com/content/fordmedia/fna/us/en/news/2017/11/09/ford-exoskeleton-technology-pilot.html.

"StrongArm Ergoskeleton Lift Assist Device V22," Strong Arm Technologies, Retrieved from the Internet on Apr. 14, 2018, 2 Pages, www. strongarmtech.com.

* cited by examiner

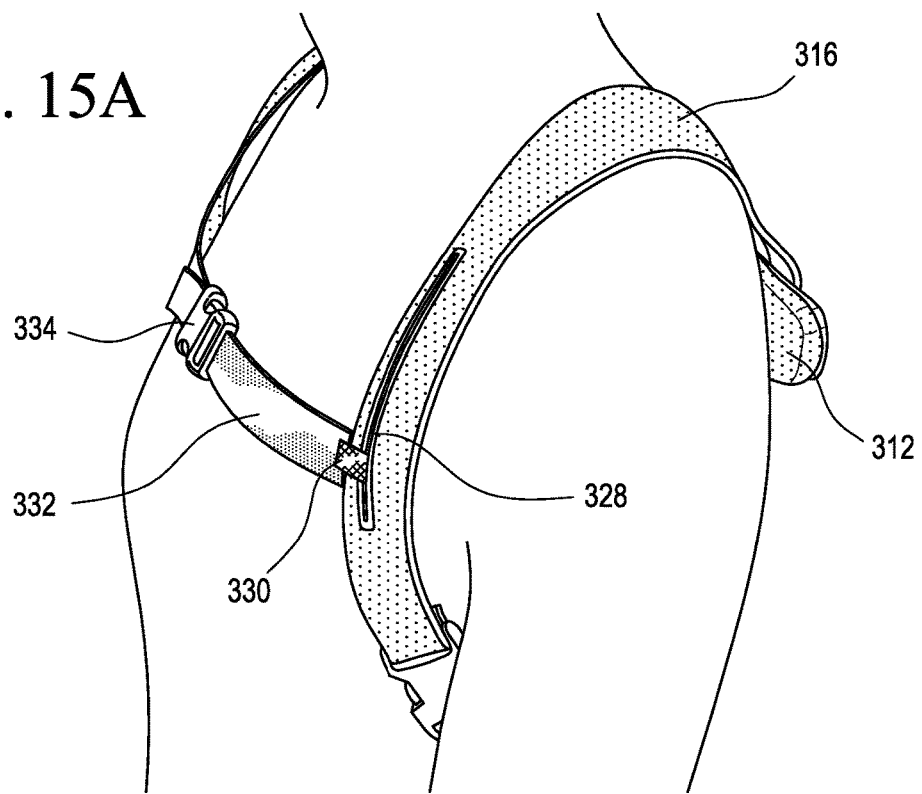
FIG. 15A
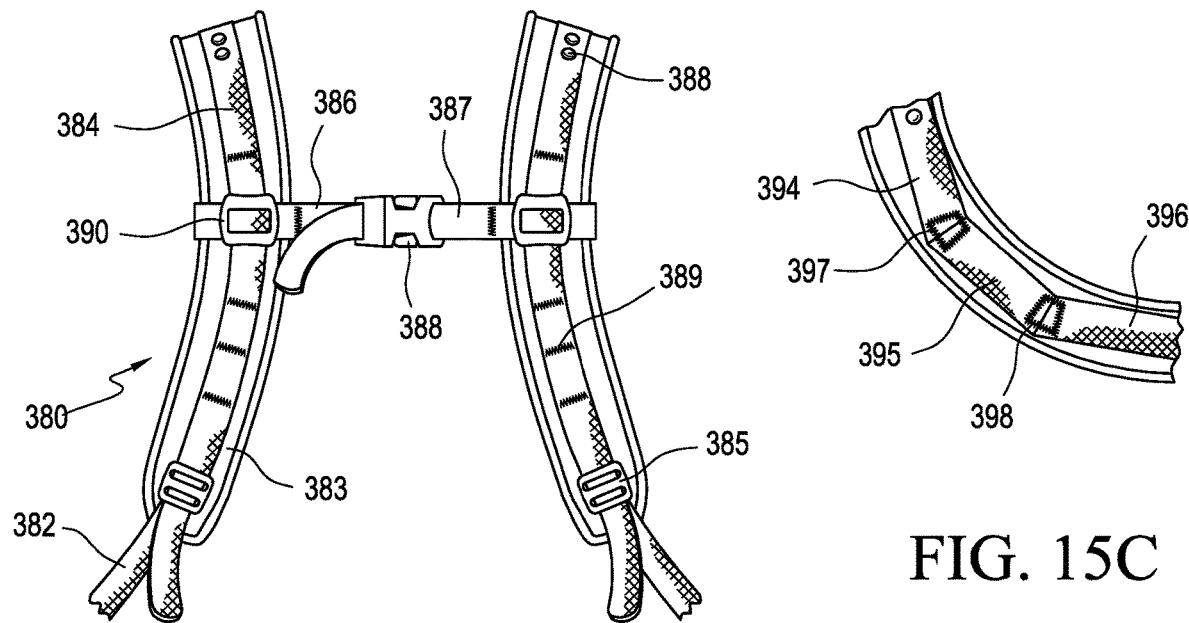
FIG. 15B
FIG. 15C

INTERFACE SYSTEM IN AN EXOSKELETON

CROSS-REFERENCE TO RELATED DISCLOSURES

This application claims the benefit of priority over U.S. Provisional Application 62/489,618, filed on Apr. 25, 2017, U.S. Provisional Application 62/583,140, filed on Nov. 8, 2017, and U.S. Provisional Application 62/590,844, filed on Nov. 27, 2017.

This application incorporates by reference U.S. Provisional Application 62/489,618, filed on Apr. 25, 2017, U.S. Provisional Application 62/583,140, filed on Nov. 8, 2017, U.S. Provisional Application 62/590,844, filed on Nov. 27, 2017, U.S. Pat. No. 9,572,705, granted Feb. 21, 2017, U.S. Pat. No. 8,657,769, granted Feb. 25, 2014, U.S. Pat. No. 8,172,779, granted May 8, 2012, and U.S. Patent Application Publication 2016/0250061, published on Sep. 1, 2016.

FIELD OF THE DISCLOSURE

The disclosure relates to an interface system for a human body in an exoskeleton, and for supporting assistive devices adapted to augment a user's performance and mitigate repetitive strain injuries.

BACKGROUND

Wearable industrial exoskeleton technologies can improve endurance and safety in industrial settings. These exoskeletons increase industrial productivity and can prevent common workplace injuries by minimizing overuse of muscles and tendons. Exoskeletons can bring support to and augment a user during strenuous activities including lifting, stooping, bending, squatting and overhead work, to reduce employee fatigue and workplace injuries. Users using such exoskeletons can effortlessly hold heavy hand tools, increasing productivity by reducing muscle fatigue.

An exoskeleton may be arranged to transfer loads through the exoskeleton to the ground in standing or kneeling positions, and allows users to use heavy tools as if they were weightless. The exoskeleton is preferably configured so it moves naturally with the body and adapts to different body types and heights.

An exemplary exoskeleton is arranged for the upper body including the shoulder and arms and increases performance by reducing forces at the shoulder, and enabling the user to perform chest-to-ceiling level tasks for longer periods of time, with less effort. The exoskeleton may assist the user to elevate and support the user's arms, and can reduce physical risks and discomfort from tasks carried out above chest height or overhead.

It has been found that lower body, trunk, and upper body regions could benefit from active exoskeletons. Muscle activity reductions have been reported as an effect of active exoskeletons. Exoskeletons have the potential to considerably reduce the underlying factors associated with work-related musculoskeletal injury. While exoskeletons are available, several technical issues hinder mainstay practical use of exoskeletons in industry. Specific issues include discomfort (for passive and active exoskeletons), the weight of the device, alignment with human anatomy and kinematics, and detection of human intention to enable smooth movement (for active exoskeletons).

Existing exoskeleton devices are too heavy, cumbersome, and difficult to adjust to a user's individual dimensions, leading to suboptimal results and discomfort. Further, many devices make use of a simplistic linear pole-like strut proximate a user's spine. This also leads to discomfort and suboptimal results as the device fails to accommodate a user's specific dimensions and to properly cooperate with the user's body.

These devices often focus more on the assistive devices as opposed to the interface between the assistive devices and the body of the user. The impact on the body by the assistive devices may therefore be sub-optimal. By considering the anatomy of the user, and how the assistive devices are located and operate relative thereto, a more useful and improved exoskeleton can be obtained by providing an interface system accommodating the action rendered by the assistive devices on the body of the user, and the biomechanics of the user's body.

The embodiments of this disclosure aim to overcome these technical issues and provide exoskeleton solutions with an improved interface system that can overcome existing problems and lead to wider adoption by industry.

SUMMARY

Embodiments of the interface system for a human body in an exoskeleton have light-weight and close-fitting components adapted to support assistive devices of the exoskeleton for augmenting a user's strength and stamina while performing repetitive tasks. The interface system embodiments can maintain the user in an ergonomically favorable body position, mitigate loads on the upper body, and stabilize against the posterior aspect of the user. The embodiments increase comfort, reduce injuries, and increase productivity of users in workplace applications by increasing speed and accuracy of tasks completed by a user.

The interface system is adapted to accommodate many user sizes, including by adjusting the posterior length and strap assembly of the interface system. As the interface system may be provided for assembly line work, workers or users of different shifts can easily adjust and comfortably secure the interface system regardless of the previous user of the interface system, assuming they fall within a general size relative to one another, as the interface system of the present disclosure can be adjusted for use by most individuals.

In an embodiment of the interface system, a posterior strut connects posteriorly to a base support having belt segments connecting on the anterior side of the user. A shoulder strap assembly connects to the posterior strut. The posterior strut has a vertical member and opposed transverse members extending from an upper end of the vertical member, and generally horizontal relative to the direction of the vertical member. The transverse members are arranged to generally extend over a user's left and right scapula.

Here, the distal foundational support of the strut/interface system is placed at the level of the sacrum posteriorly, and the anterior superior iliac crest (ASIC) or waist anteriorly. The posterior strut can resist the torque applied to it by the attached assistive devices. The torque would, without stabilization, rotate the posterior strut and panel of a base support posteriorly away from the body. A cinchable waist belt is attached to the panel, combining as the base support, which wraps around the anterior aspect of the body forming the counter force for the torque placed on the posterior strut. The long posterior strut concept reduces the posteriorly-directed felt force on the anterior body in combination with the base support, and creates lumbar support. The long posterior strut, appropriately contoured, also provides lumbar support, resisting lumbar flexion if the user is lifting an object.

The posterior strut may also be arranged with a shorter height over known spinal frames. The shortened posterior strut similarly locates its transverse members over the scapula. The length of the vertical member may be shortened distally because it positions the base support at or just above the inferior costal margin (ICM) of the user. The distal foundational support of the strut/interface system is placed at the ICM, allowing greater freedom of movement in the lumbar spine. Here, the supportive cinching belt (and assistive torque counterforce) is at the level of the ICM. The shorter-felt force against the anterior body is greater due to the shorter lever arm of the strut, but this may also free lumbar spinal range of motion up if so desired. In this configuration, while the user is more free to move in certain ways, the lumbar spine is not offered protection through ROM limitation.

In both versions, a horizontal strut component or transverse member is located approximately at the level which sets the assistive joint at the level of the anatomical shoulder joint or the humeral head. In a longer form of the posterior strut, the base support is positioned at the waist, which transfers the load from the arm support to the lower pelvis while promoting healthy posture. In a short version of the posterior strut, the load from the arm support is transferred to the lower ribs while freeing up the waist for flexion, lateral bending and rotation to perform necessary tasks with minimal restriction.

From the standpoint or objective of lifting objects, which the assistive device is used to supplement, the arrangement of the posterior strut in the long version, restricts excessive lumbar flexion, once fully donned on the user. A user is less likely to have rotational twist of the spine, and less likely to excessively flex the spine while lifting if using the long version. This has the benefit of forcing a user to use their legs more while lifting an object, particularly in combination with the assistive device(s), which reduces back injury risk and improves stamina.

By the arrangement of the posterior strut in the short version, the posterior strut transfers the load created by the assistive device to the lower ribs of the user while freeing up the user's waist for flexion, lateral bending, and rotation to enable the user to perform necessary tasks with minimal restriction, overall increasing mobility for the user over the long version while still providing the aid of the assistive device.

These and other features, aspects, and advantages of the present disclosure will become better understood regarding the following description, appended claims, and accompanying drawings.

BRIEF DESCRIPTION OF THE DRAWINGS

FIG. 15A is a front perspective view of the embodiment of FIG. 14.

FIG. 15B is a schematic view of a variation of the chest strap in FIG. 15A.

FIG. 15C is a schematic view of a variation of the chest strap in FIG. 15B.

Figure 1:
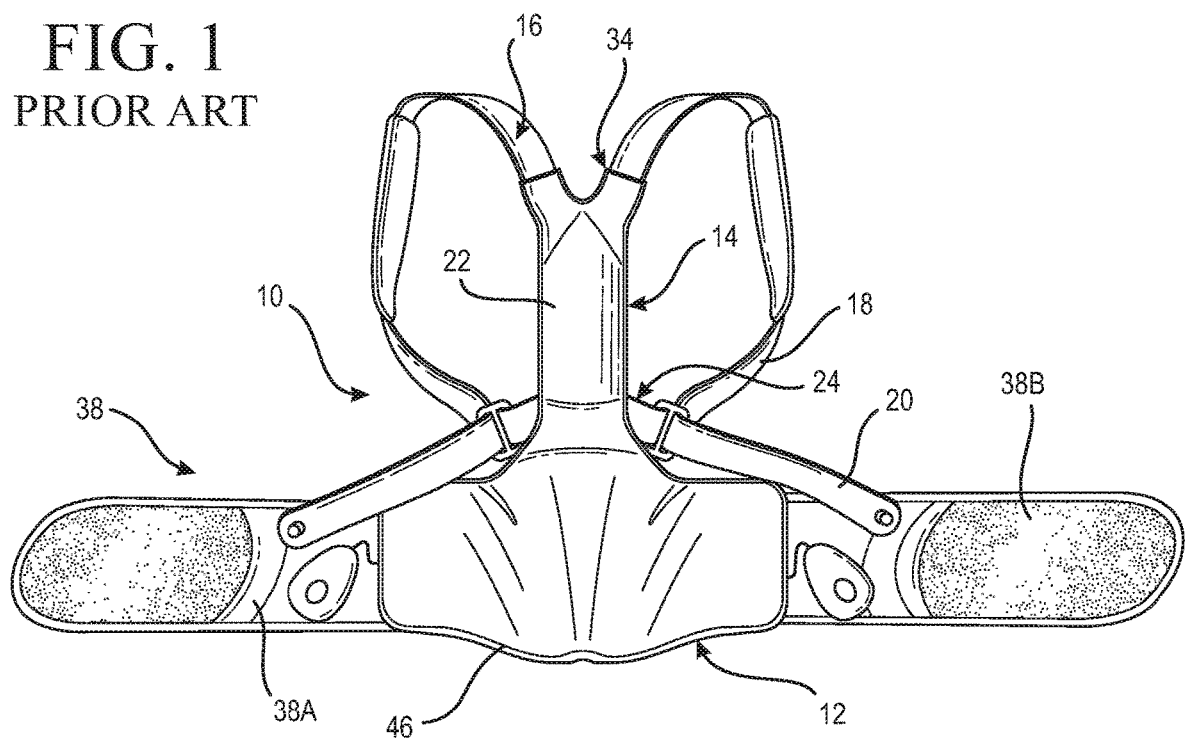
FIG. 1 is an elevational view of a prior art spinal orthosis.

The drawing figures are not drawn to scale, but instead are drawn to provide a better understanding of the components, and are not intended to be limiting in scope, but to provide exemplary illustrations.

DETAILED DESCRIPTION OF VARIOUS EMBODIMENTS

A. Overview

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the embodiments of an interface system and variants as disclosed, a description of a few terms is necessary. As used, the term "proximal" has its ordinary meaning and refers to a location next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Last, the term "anterior" has its ordinary meaning and refers to a location ahead of or to the front of another location.

These anatomical terms follow the user wearing the interface system referring to an anatomical position. An anatomical position is generally defined as the erect position of the body with the face directed forward, the arms at the side, and the palms of the hands facing forward, and which is a reference in describing the relation of body parts to one another.

The terms "rigid," "flexible," "compliant," and "resilient" may distinguish characteristics of portions of certain features of the interface system. The term "rigid" should denote that an element of the interface system, such as a frame, is generally devoid of flexibility. Within the context of features that are "rigid," it should indicate that they do not lose their overall shape when force is applied, and may break if bent with sufficient force. The term "flexible" should denote that features are capable of repeated bending such that the features may be bent into retained shapes or the features retain no general shape, but continuously deform when force is applied.

The term "compliant" may qualify such flexible features as generally conforming to the shape of another object when placed in contact therewith, via any suitable natural or applied forces, such as gravitational forces, or forces applied by external mechanisms, for example, strap mechanisms. The term "resilient" may qualify such flexible features as generally returning to an initial general shape without permanent deformation. As for the term "semi-rigid," this term may connote properties of support members or shells that provide support and are free-standing; however, such support members or shells may have flexibility or resiliency.

The embodiments of the disclosure are adapted for a human body, and may be dimensioned to accommodate different types, shapes, and sizes of human body sizes and contours. For explanatory purposes, the interface system embodiments described correspond to different sections of a body and are denoted by general anatomical terms for the human body.

The embodiments of the interface system may correspond to anterior and posterior body sections defined by an anterior-posterior plane. The anatomical terms described are not intended to detract from the normal understanding of such terms as readily understood by one of ordinary skill in the art of orthopedics, braces, human interfaces, and supports.

B. Prior Art Spinal Orthosis

For an understanding of the interface system of the disclosure, it is acknowledged that it builds from the spinal orthosis discussed in U.S. Pat. No. 9,572,705, and illustrated by convenience in FIGS. 1 and 2.

Figure 2:
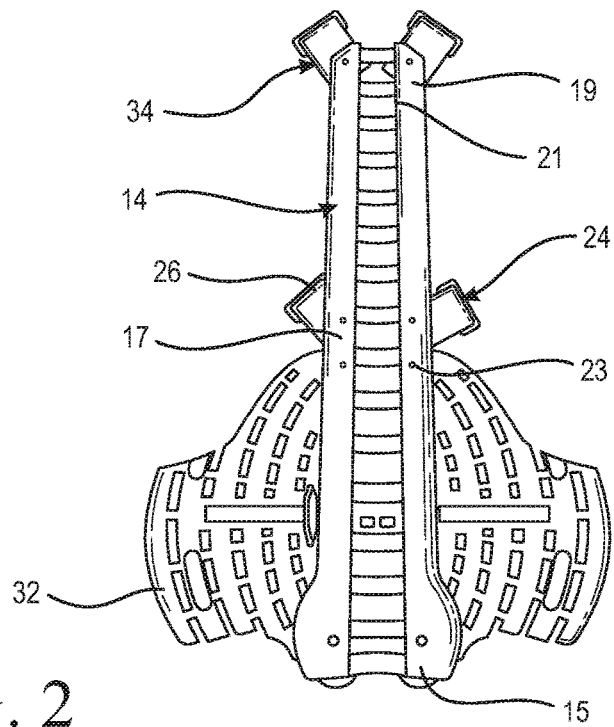
FIG. 2 is an exemplary interior view of a posterior frame system in the spinal orthosis of FIG. 1.

According to FIGS. 1 and 2, the spinal orthosis 10 is provided for, among other functions, increasing trunk muscle strength and improving posture in individuals with vertebral fractures.

The spinal orthosis 10 includes a lumbar device 12, as in U.S. Pat. No. 8,172,779 and U.S. Patent Application Publication 2016/0250061, a posterior frame system or spinal frame 14, and a strap assembly 16. The strap assembly 16 includes straps 18 that engage an upper bracket system 34 at a portion of the spinal frame 14 near or at the posterior shoulders and extend over the shoulders and under the armpits to orient a middle bracket system 24 on a middle portion of the spinal frame 14. The straps 18 are redirected by brackets 26 carried by the middle bracket system 24 toward the anterior side of the lumbar device 12 whereat the strap ends 20 secure to the surface of the lumbar device 12.

The strap assembly 16 permits downward pulling of the straps 18 at a location, such as the waist or abdomen, which is easier for a geriatric individual to pull than at the shoulders, as in many prior art orthoses. Users of the orthosis 10 that are arthritic or have poor dexterity need only pull down the straps 18 at a location roughly below the chest to tighten the strap assembly 16 over the shoulders. They may similarly attach the strap ends 20 to the lumbar device 12 at a relatively low location that is comfortable and easy for the user to manipulate.

Both the closure system of the lumbar device 12 and the spinal frame 14 may be covered by suitable sleeves or covers 22, 46 to cushion and conceal these various features, leading to an aesthetically pleasing and comfortable arrangement. The lumbar device 12 includes first and second belt segments 38A, 38B (collectively 38) which permit easy donning of the lumbar device 12 over the waist. Suitable additional padding may be provided along the strap assembly 16 over the shoulders to provide compressive relief to the user when the strap assembly 16 is tensioned, or along the spinal frame 14 and lumbar device 12.

The posterior frame system includes the spinal frame 14 defining an elongate frame having a lower portion 15 corresponding to and extending from a lower portion of a lumbar panel or support 32, such as a flexible or semi-rigid plate or frame, a middle portion 17 above the lumbar support 32 and carrying the bracket system 24, and an upper portion 19 carrying an upper bracket system 34. The spinal frame 14 defines a plurality of openings 21 along its length, and is fixedly secured to the lumbar support 32 by a plurality of fasteners 23. The spinal frame 14 may have a profile, as shown in FIG. 2, in which the lower portion 15 flares outwardly and the spinal frame 14 narrows in width as it approaches the upper portion 19 to anatomically better conform to the user's anatomy.

The spinal frame 14 is constructed from a malleable aluminum which can be shaped by a practitioner according to the individual anatomy of a user. The lumbar panel 32 of the lumbar device 12 may be formed from a plastic that is flexible relative to the spinal frame 14. Lateral side portions of the lumbar panel 32 may flex relative to the spinal frame 14. While the spinal frame 14 can be shaped according to an individual's anatomy, it provides additional rigidity to ensure that the user's back can be pulled into extension. The spinal frame 14 may be formed by injection molding a plastic covering over the metal strut.

C. Embodiments of the Interface System

Figure 3:
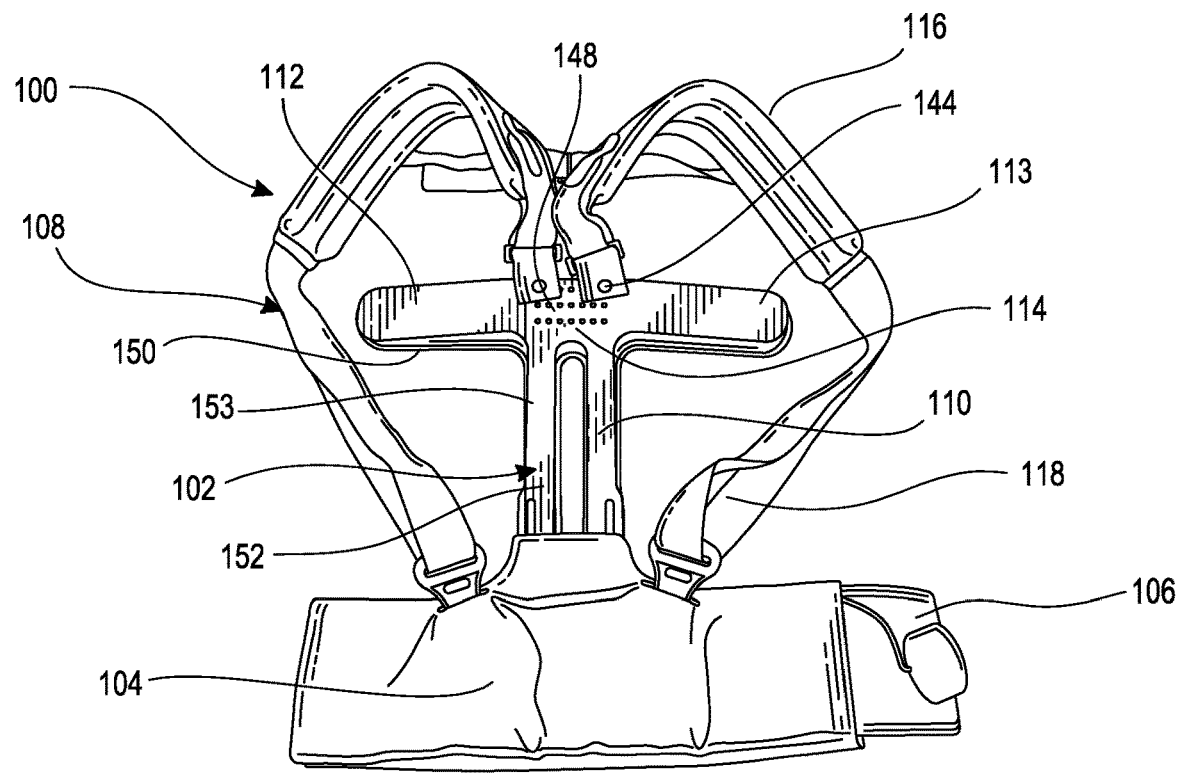
FIG. 3 is a schematic view of an embodiment of a wearable interface system.

FIG. 3 depicts an embodiment of the interface system 100 having a posterior strut 102 connecting to a base support 104 having belt segments 106 connecting on the anterior side of the user. The base support 104 may be modified from the lumbar device 12, to accommodate the posterior strut 102 and offer additional features and advantages over the known lumbar device 12. A shoulder strap assembly 108 connects to the posterior strut 102, and to the base support 104.

The posterior strut 102 has a vertical member 110 and opposed horizontal strut component or transverse members 112, 113 extending from an upper end of the vertical member 110, and arranged perpendicular, horizontal, or transverse relative to the direction of the vertical member 110. The transverse members 112, 113 are arranged to generally extend over a user's left and right scapula S. The vertical member 110 has a widened configuration with a width $W_{VM}$ arranged to transfer loads over the user's spine, and is substantially wider than a width $W_{HM}$ of the transverse members 112, 113 which extend away from the vertical member 110 in opposed directions, as shown in more detail in FIGS. 9A and 9B.

Of particular distinction over the prior art spinal orthosis 10, the posterior strut 102 of interface system 100 replaces the spinal frame 14 of the spinal orthosis 10. The posterior strut 102 is arranged with a shorter height over the spinal frame 14. The posterior strut 102 is shortened to locate its transverse members 112, 113 extending from the vertical member 110 at the spine of the scapula S, as evidenced in FIG. 9A. The height of vertical member 110 is set to create a concentric relationship between the humeral head and the rotational axis 120 in the coronal plane in FIG. 7A. The length of the vertical member 110 is likewise shortened distally because it positions the base support 104 at or just above the ICM of the user, as in a short version of the interface system.

Figure 9A:
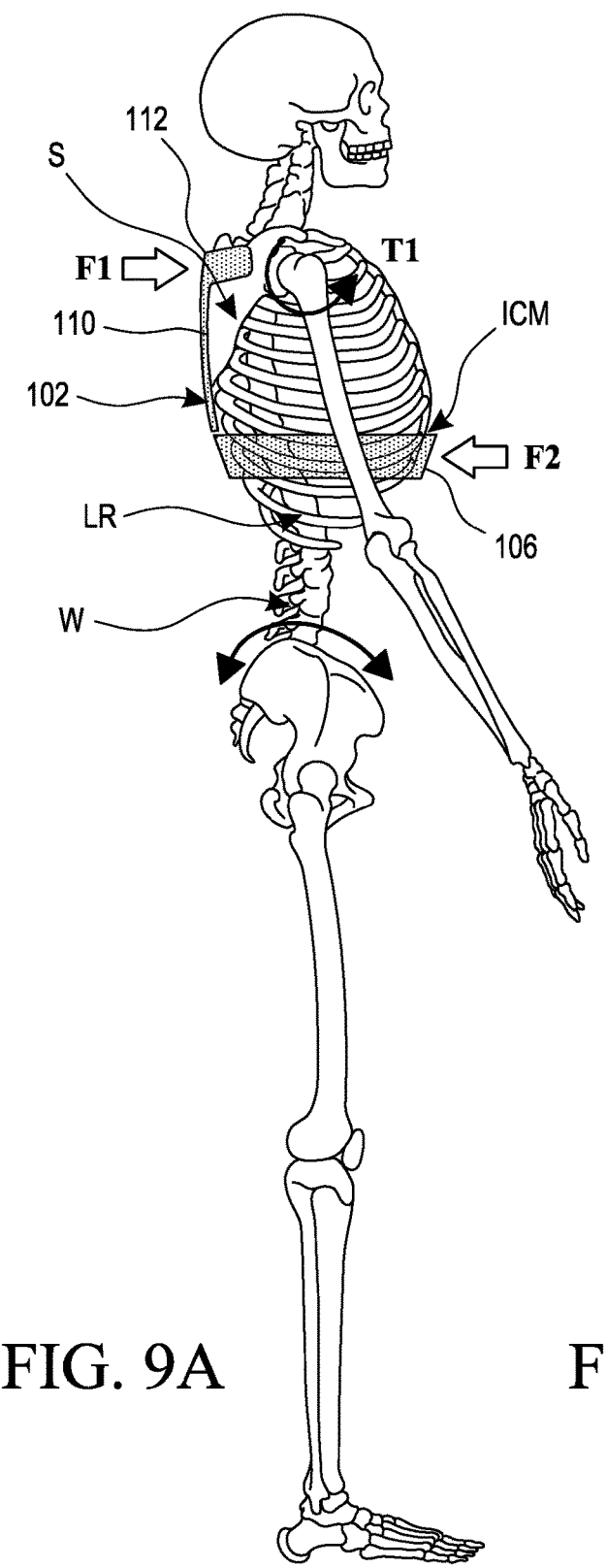
FIG. 9A is a schematic view of a short version of the interface system of FIG. 3 on a skeleton.
Figure 9B:
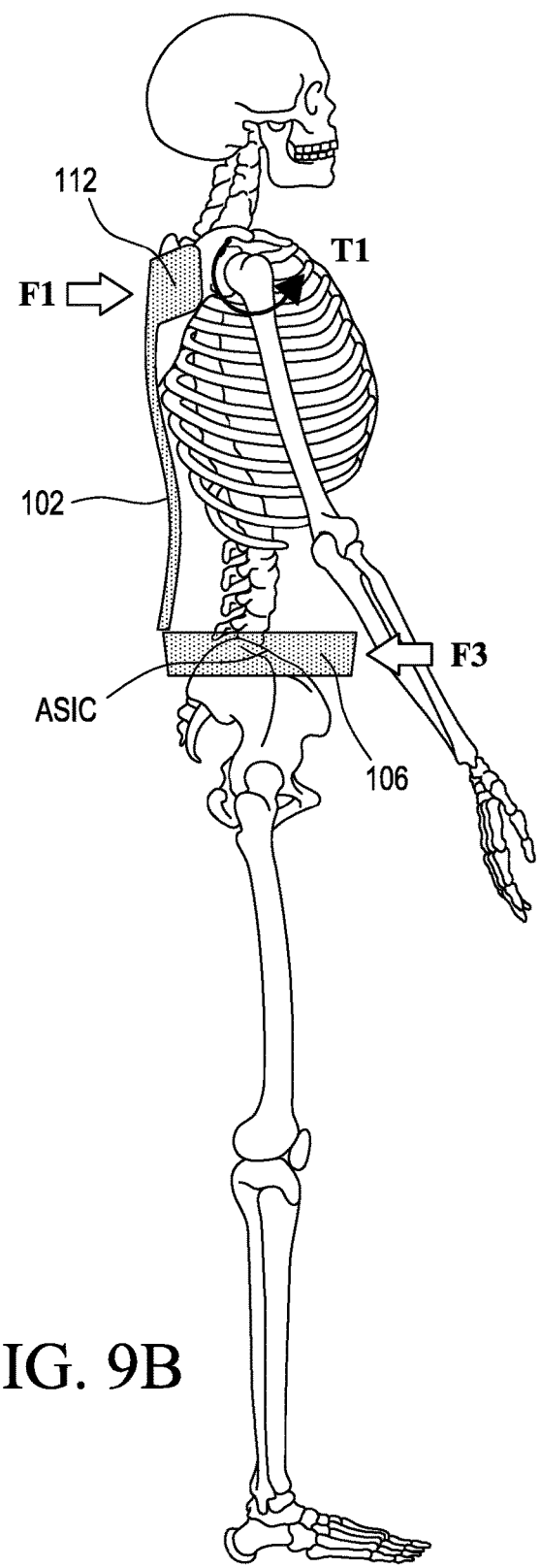
FIG. 9B is a schematic view of a long version of the interface system of FIG. 3 on a skeleton.

FIGS. 9A and 9B show how there can be a short and a long version of the interface system. In both versions, a horizontal strut component is located approximately at the level which sets the assistive joint at the anatomical shoulder joint. In the long version (FIG. 9B), the base support is positioned at the waist, which transfers the load from the arm support to the lower pelvis while promoting healthy posture. The short version (FIG. 9A) transfers the load from the arm support to the lower ribs while freeing up the waist for flexion, lateral bending, and rotation to perform necessary tasks with minimal restriction.

From the standpoint or objective of lifting objects, which the assistive device is used to supplement, the arrangement of the posterior strut 102 in the long version of FIG. 9B restricts excessive lumbar flexion, once fully donned on the user. A user is less likely to have rotational twist of the spine, and less likely to excessively flex the spine while lifting if using the long version of FIG. 9B. This has the benefit of forcing a user to use their legs more while lifting an object, particularly in combination with the assistive device, which reduces back injury risk.

According to the arrangement in FIG. 9B, the distal foundational support of the strut/interface system is placed at the level of the sacrum posteriorly and the ASIC anteriorly. The strut can resist the torque applied to it by the attached assistive devices. The torque would, without stabilization, rotate the posterior strut and panel posteriorly away from the body, as evidenced by force F1 and torque T1. A cinchable waist belt is attached to the panel which wraps around the anterior aspect of the body forming the counter force, by force F3, for the torque placed on the posterior strut. The long posterior strut reduces the posteriorly directed felt force F3 on the anterior body. The long contoured strut also provides lumbar support, resisting lumbar flexion if the user is lifting an object.

Figure 7A:
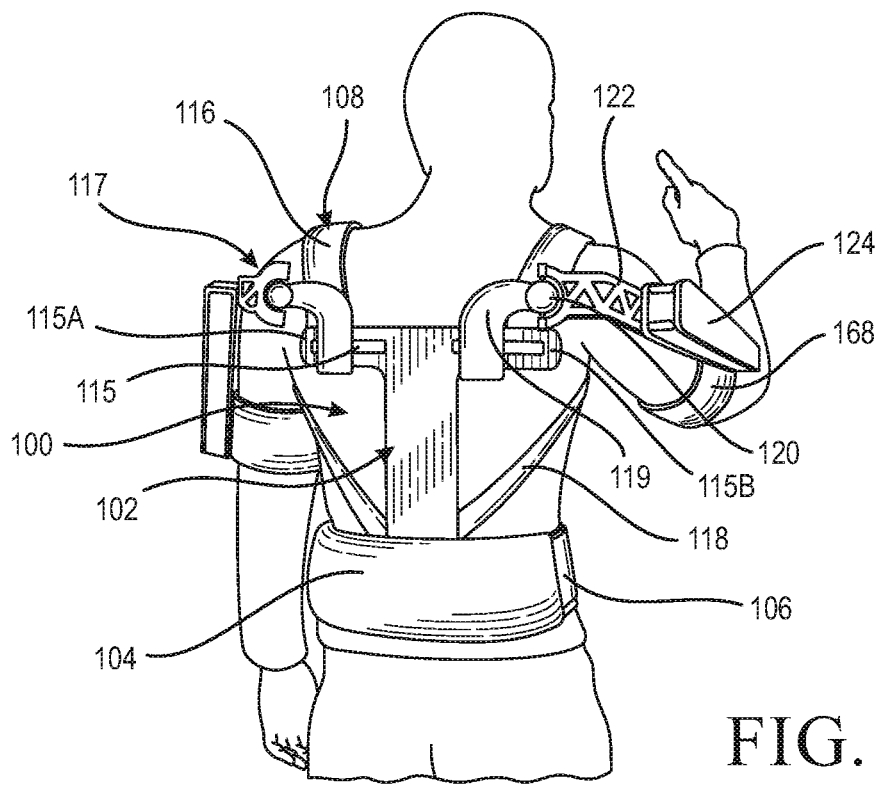
FIG. 7A is a schematic posterior view of an individual wearing a variation of the interface system of FIG. 3 and an assistive device.
Figure 7B:
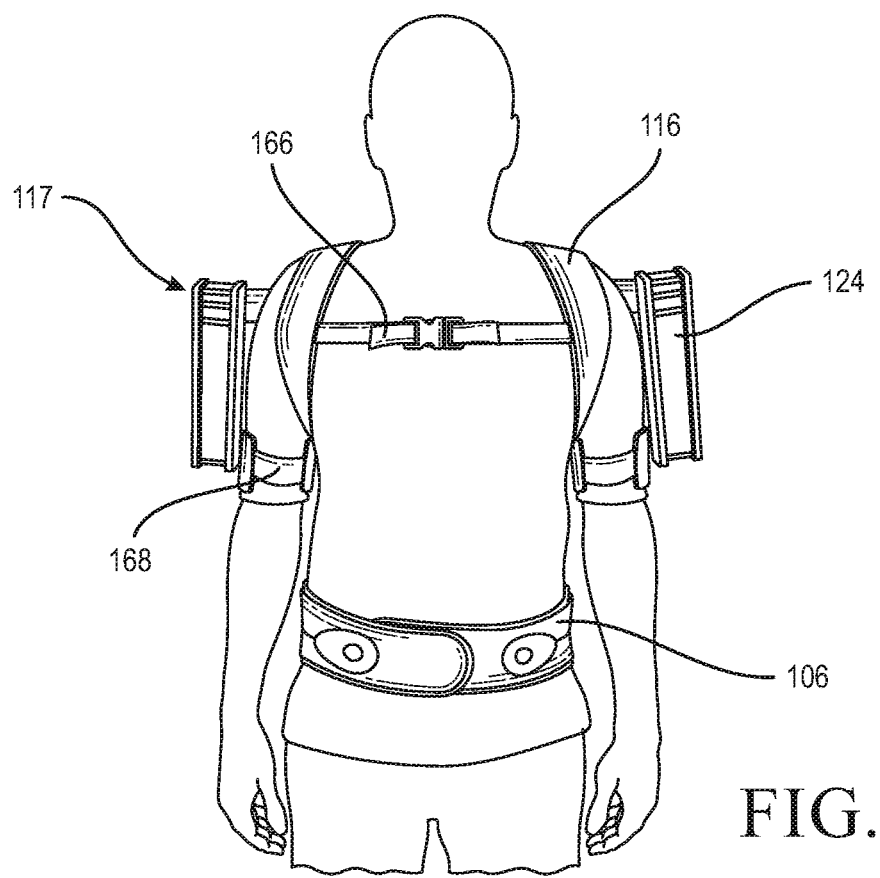
FIG. 7B is a schematic anterior view of an individual wearing the interface system of FIG. 3 and an assistive device.

By the arrangement of the posterior strut 102 in the short version of FIG. 9A, the posterior strut 102 transfers the load created by the shoulder assist mechanism 117 of FIGS. 7A and 7B to the lower ribs (LR) of the user while freeing up the user's waist (W) for flexion, lateral bending, and rotation to enable the user to perform necessary tasks with minimal restriction. This arrangement overall increases mobility for the user over the long version of FIG. 9B, while still providing shoulder flexion assistance.

In this embodiment, the posterior strut 102 may also be arranged with a shorter height over known spinal frames. The posterior strut 102 similarly locates its transverse members 112, 113 over the scapula. The length of the vertical member 110 may be shortened distally because it positions the base support at or just above the ICM of the user. The distal foundational support of the strut/interface system 100 is placed at the ICM, allowing greater freedom of movement in the lumbar spine. Here, the base support (and assistive torque counterforce) is at the level of the ICM. The shorter-felt force of force F2 countering force F1 and torque T1 against the anterior body is greater due to the shorter lever arm of the posterior strut 102, but this may also free up lumbar spinal range of motion if so desired, as this combination of features may be advantageous for certain uses, such as when heavy lifting is not anticipated but rotational movement must be accommodated. In this configuration, while more free toward certain movements, the lumbar spine is not offered protection through ROM limitation.

Returning to FIG. 3, the base support 104 preferably has a narrower height than the lumbar device 14 in the spinal orthosis 10. The narrower height may be defined by a height of the belt segments 106. The base support 104 in combination with the posterior strut 102 presents an overall shortened height compared to the spinal orthosis 10. The shortened height enables a load transmission to the user's ribs while leaving the breast and pectoralis regions free for increased mobility by the user during normal tasks.

The shoulder strap assembly 108 includes a shoulder strap having a first segment 116 extending over the shoulder and a second segment 118 for attachment on the base support 104, as in the spinal orthosis 10. However, due to the attachment of a shoulder assist mechanism 117, as shown in FIG. 7A, the strap assembly 108 is routed differently about the user's shoulders by the first segment 116 than in the spinal orthosis 10.

FIG. 3 exemplifies how the posterior strut 102 has a center portion 114 between the transverse member 112, 113 whereat brackets 144 of the first segment 116 of the shoulder strap assembly 108 secure. The center portion 114 defines a plurality of openings 148, at any of which one of the brackets 144 may secure. The openings 148 extend in rows along the horizontal and vertical directions to enable the strap assembly 108 to be easily and conveniently customized for different users' dimensions. The second segment 118 of the strap assembly 108 has brackets that secure to the base support 104.

Suitable padding 150 may line at least an interiorly-facing section of the posterior strut 102 directly adjacent and facing a user's body for enhanced comfort, breathability, and user compliance. The padding 150 may be overmolded onto the posterior strut 102, or may comprise a removable element to facilitate cleaning, replacement, or user customization of the padding 150.

Figure 4:
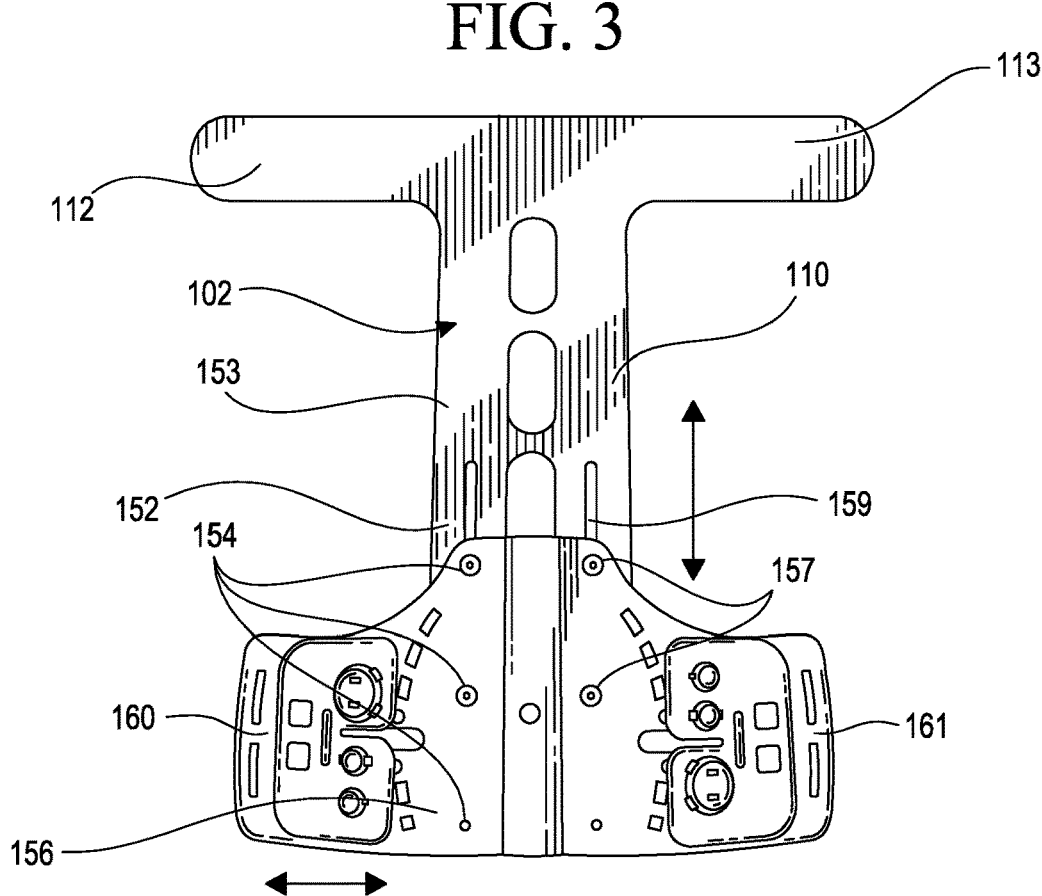
FIG. 4 is a schematic view of the interface system of FIG. 3 having a posterior strut adjustable relative to a lower support.

Referring to FIGS. 3 and 4, the posterior strut 102 defines a lower section 152 that connects to a panel 156 of the base support 104. FIG. 3 depicts how the lower section 152 may have a wider width than a width of an intermediate section 153 directly above the lower section 152 to minimize the area the posterior strut 102 covers over the user's spine and to reduce the weight of the interface system 100. The lower section 152 may be wider than the intermediate section 153, by, for example, a 7:8 ratio.

The posterior strut 102 is slidably adjustable in height relative to the base support 104. The panel defines a plurality of apertures 154 aligned to vertical side slots 159 of the lower section 152 of the posterior strut 102. Fasteners 157 may be secured about any of the apertures 154 according to the height setting of the posterior strut 102 to engage and secure the lower section 152 about vertical side slots 159. The panel defines first and second wings 160, 161 extending generally laterally from the lower section 152 for providing additional support to the base support 104, and for distributing compression and anchoring of the interface system 100 about a user's waist or lower back. This arrangement disperses pressure on the user, especially in the shortened configuration enhancing comfort and user compliance.

The posterior strut 102 can be attached to the base support 104 by having a plurality of channels or slots, whereby a push button or similar adjustment permits convenient and intuitive vertical adjustment of the posterior strut 102.

Figure 5:
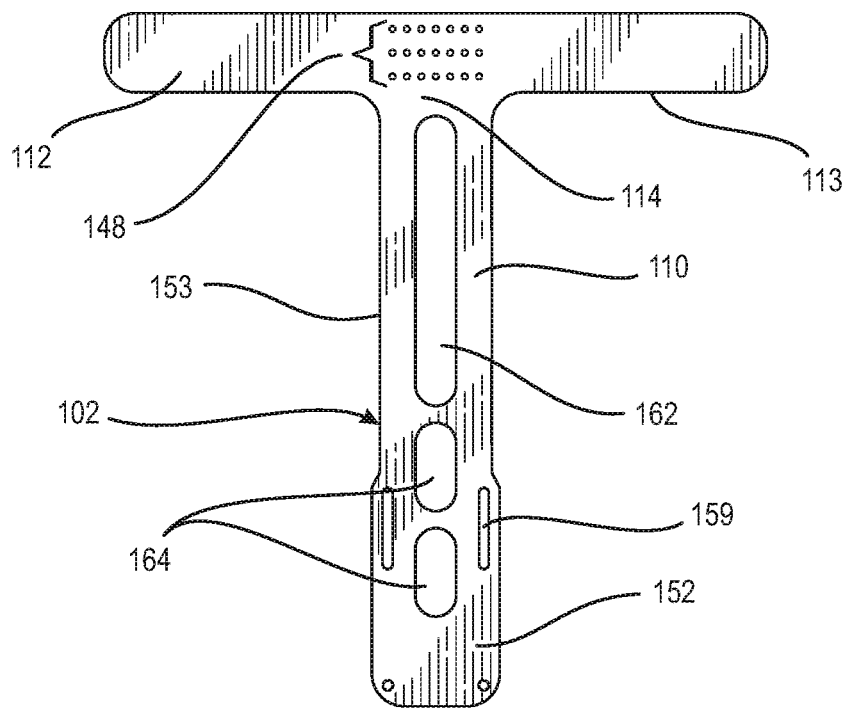
FIG. 5 is a plan view of the posterior strut in the interface system of FIG. 3.
Figure 6:
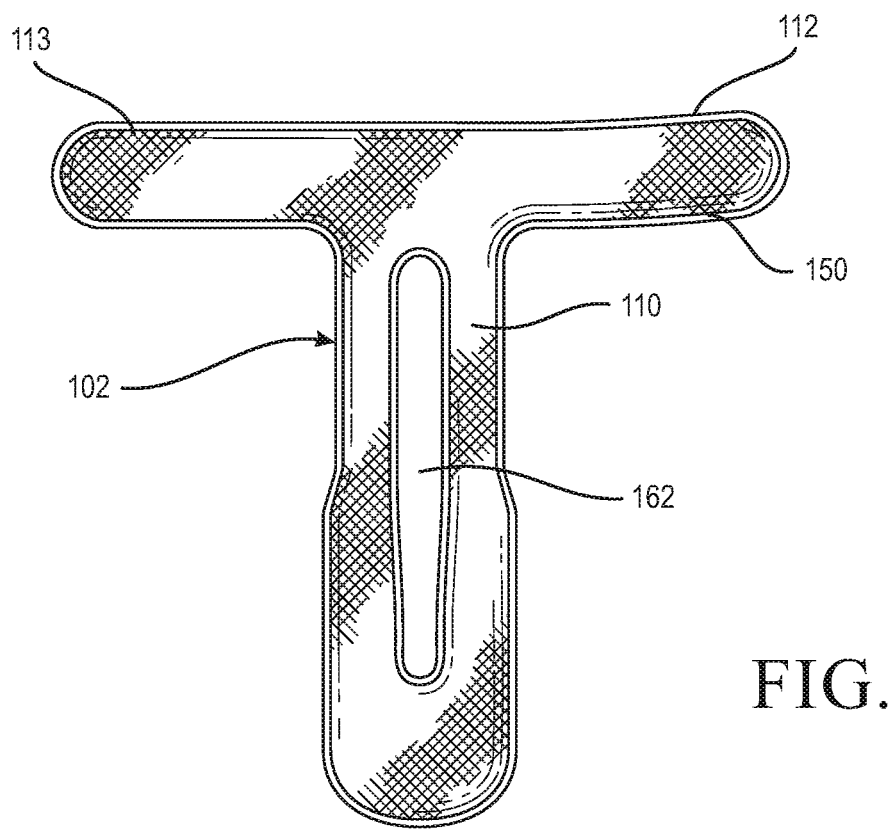
FIG. 6 is a plan view of a variation of the posterior strut of FIG. 5 with a cover.

FIGS. 5 and 6 are detailed views of the posterior strut 102 of FIG. 3, whereby some features are discussed above. The posterior strut 102 is arranged in a thin and breathable manner to provide minimal coverage over the user's body and to minimize weight. The posterior strut 102 defines an elongate vertical opening 162 generally corresponding to the user's spine, and permitting contouring, as discussed with the embodiment of FIGS. 10 and 11. The posterior strut 102 defines lower openings 164 which may yield a stiffer region for contouring of the posterior strut 102 relative to the intermediate section 153. Preferably, the lower section 152 extends to the waist.

The intermediate section 153 of the posterior strut 102 allows for deflection in the sagittal plane for added "springiness," and permits a degree of transverse plane torsion, both of which provide functional comfort through many activities. The posterior strut 102 may be overmolded with a tough yet softer material than the material forming the posterior strut 102 to provide enhanced comfort to the user. According to this embodiment of the posterior strut 102, there is a baseline strength of the posterior strut 102 to offer sufficient stiffness but also allow yield both in sagittal and transverse planes when loaded by bilateral shoulder assist devices. Dimensions of the posterior strut 102 in combination with the material properties can be reduced in size and weight to a minimum, while providing a certain desired level of deformation and stiffness.

FIGS. 7A and 7B exemplify the industrial exoskeleton or shoulder assistive device 117 on the interface system 100. The assistive device 117 has support frames 119 attached to each of the free end portions 115A, 115B of the transverse members 112, 113 via horizontal slots or connection elements attached to or defined by the transverse members 112, 113. As the width and height of a user's shoulders vary based on each individual, the assistive device 117 may translate within the horizontal slots to position the attachment of the assistive device 117 between the support frames 119 and the transverse members 112, 113 proximate the user's humeral head.

The support frames 119 may include articulation devices 120 for the assistive device 117, and connectors 122 for attaching to the first segment 116 of the strap assembly 108. The connectors 122 may be extended vertically along the user's upper back and over the shoulder to the anterior side. The connectors 122 may comprise a rigid or semi-rigid frame, as in FIG. 3, or may be formed as an extension of the first segment 116 which can secure directly to the support frames 119. Assist mechanisms 124 are supported by the connectors 122 for offering mechanized assistance for lifting/flexion by the shoulders, and may include an actuator mechanism to provide humeral flexion assistance.

As shown in FIGS. 7A and 7B, the interface system 100 may have arm cuffs 168 for supporting the connectors 122 on a user's arms, and a sternum strap 166 to better harness the assistive device 117 on the user.

Figure 8A:
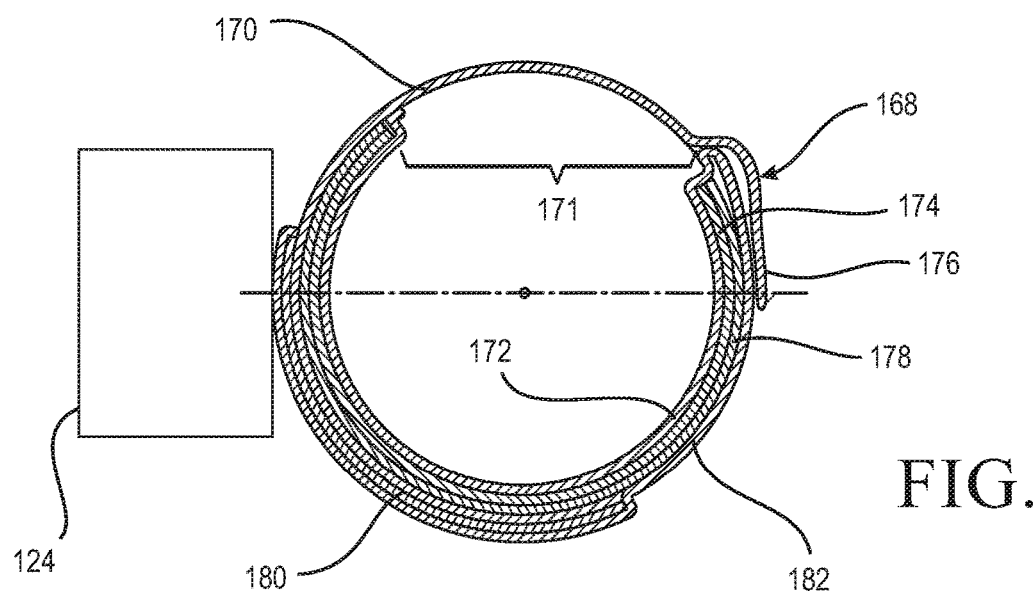
FIG. 8A is a schematic view showing an embodiment of an arm cuff in the interface system of FIG. 3.
Figure 8B:
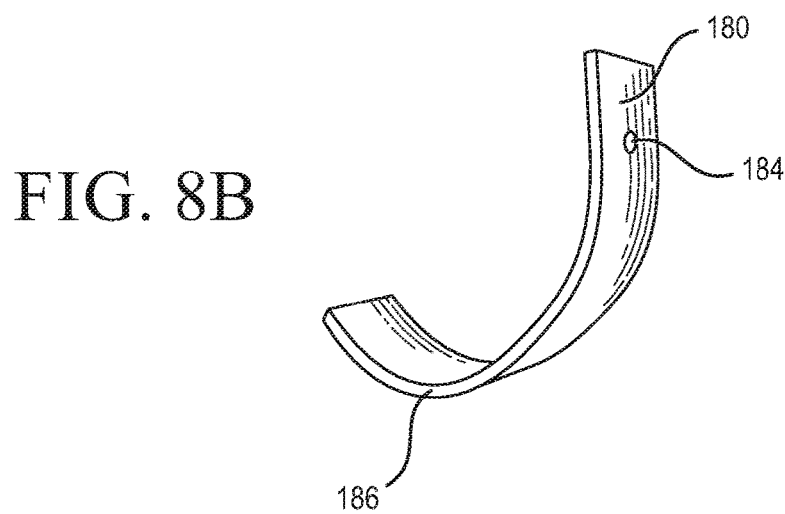
FIG. 8B is a perspective view of a malleable band useable in the arm cuff of FIG. 8A.
Figure 8C:
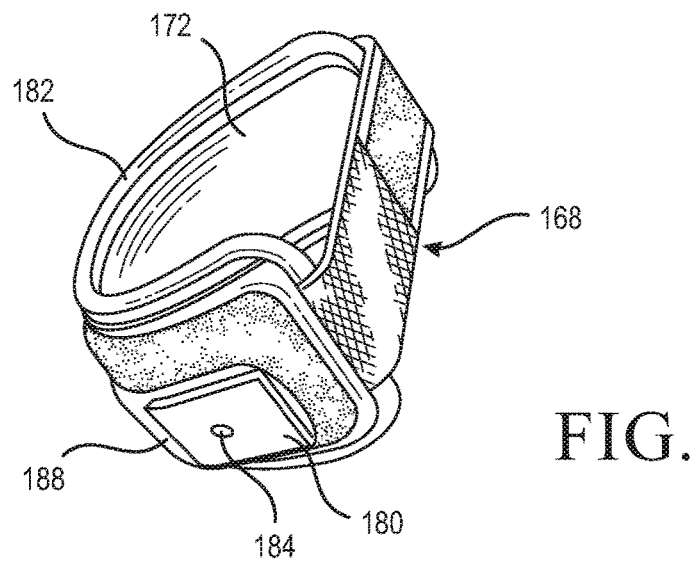
FIG. 8C is a perspective view of a variation of the arm cuff of FIG. 8A.

FIGS. 8A through 8C exemplify embodiments of the arm cuffs 168. As the assistive device 117 may provide humeral flexion assistance, the assist mechanism 124 may be attached to the arm cuffs 168, which affix generally to the humerus. These arm cuffs 168 are adjustable to accommodate a considerable size range of users' arms, and adjust relative to girth changes suitable for potential users and as a user's arm changes dimensions during contraction.

FIG. 8A shows a cross-sectional view of an exemplary arm cuff 168. The arm cuff 168 includes a closure strap or band 170 having elastic properties to accommodate a change in girth of the arm due to contraction. The closure strap 170 extends and is suspended across a gap 171 formed by the arm cuff 168. The closure strap 170 permanently secures at a first side of the gap 171 to the arm cuff 168, and removably secures at a second end of the arm cuff 168 to a fastener, such as a hook and loop fastener 176, carried by an outer layer 182 of the arm cuff 168. The gap 171 permits the arm cuff 168 to accommodate the change in girth of the user's arm by receiving the increased volume of the arm in the gap while still securely retaining the assistive device 117 on the user by the elastic closure strap 170 which remains in engagement with the arm.

The arm cuff 168 has an inner layer formed from layer 172 enclosing a pad 174 adapted to be adjacent to and surround the user's humerus. The pad 174 may be a foam layer extending along and lining an entirety of the arm cuff 168 aside from a gap 171. External to the pad 174 is a reinforcing layer 178 of semi-rigid plastic, flexed about the user's arm but remaining rigid once the closure strap 170 is secured about a user's arm. The reinforcing layer 178 maintains the cuff shape while minimizing the pressure felt at the end of the closure strap 170.

A malleable band 180 is adjacent the reinforcing layer 178, and preferably only extends along about 20% to 40% of the circumference of the arm band 168. The malleable band 180 is secured to the assist mechanism 124 and preferably wraps about the posterior aspect of the user's arm, particularly when it is desirable that the assistive device 117 suspends the arms in an upright position as the arm cuff 168 then provides optimal support to a user. The malleable band 180 preferably attaches lateral to the humerus and passes under the humerus pointing medially. The extent by which the malleable band 180 extends about the arm cuff 168 provides sufficient support behind the humerus while allowing the arm cuff 168 to comfortably flex against a chest wall of the user.

As shown in FIG. 8B, the malleable band 180 has at least one affixation point 184, which may be defined by an aperture, for securing to the assist mechanism 124. The malleable band 180 can be modified by a user or a clinician from a predetermined profile 186 to accommodate a shape of an individual user's arm.

FIG. 8C exemplifies how the arm cuff 168 defines a channel 188 formed by the outer layer 182 of the arm cuff 168. The channel 188 extends through a length about the arm cuff 168 short of the length of the reinforcing layer 178. The channel 188 is adapted to removably receive the malleable band 180, wherein the at least one fixation point 184 may extend outside of the arm cuff 168 for affixation to the assist mechanism 124. An opening may be formed by the outer layer 182 that enables engagement of the assist mechanism 124 to the malleable band 180. The channel 188 minimizes shear and sliding of the malleable band 180 of the arm cuff 168, and allows for removal of the malleable band 180 for cleaning and/or adjustment.

As discussed, at least a portion of the malleable band 180 is preferably exposed through the outer layer 182 to facilitate mounting of an assistive device 124, as shown in FIG. 8C, particularly where the at least one fixation point 184 is located. The outer layer 182 may conceal the malleable band 180, as shown in FIG. 8A.

Figure 10:
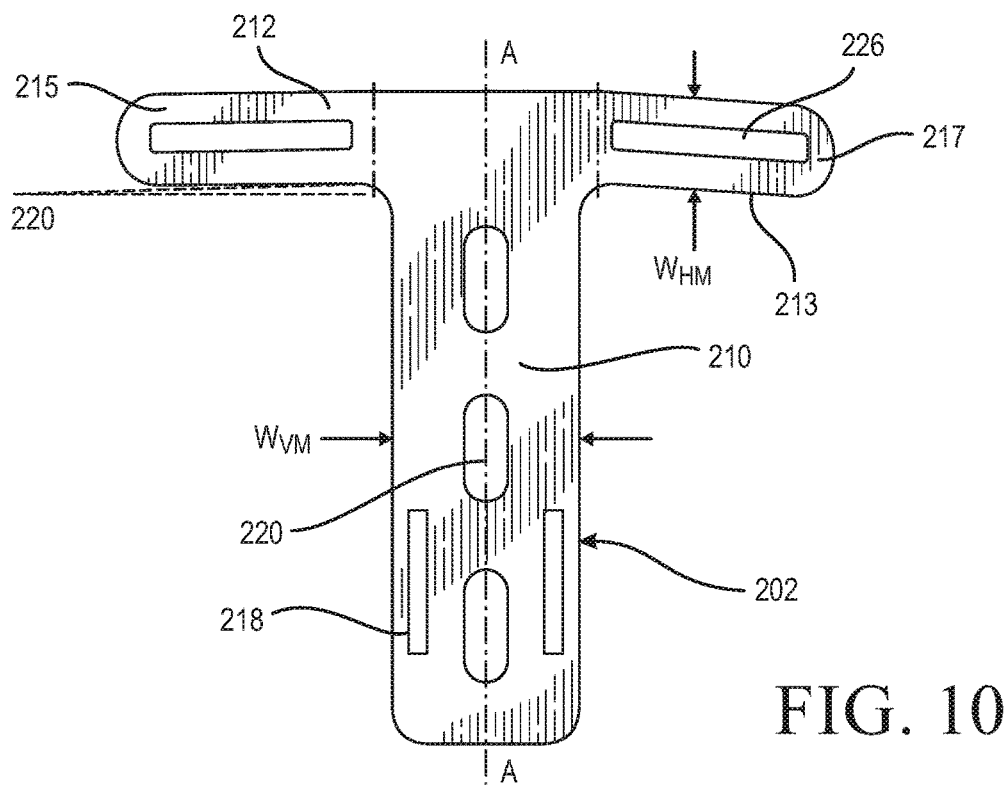
FIG. 10 is an elevational view of another variation of the posterior strut for the interface system of FIG. 3.
Figure 11:
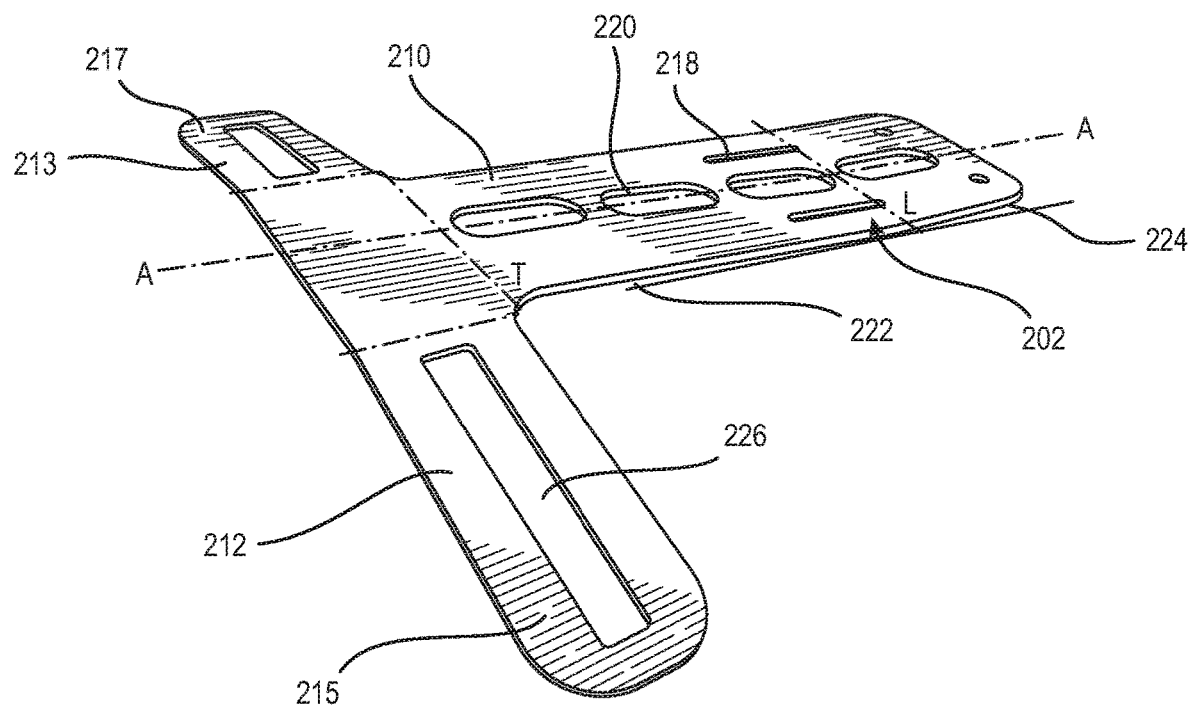
FIG. 11 is a schematic perspective view showing the posterior strut of FIG. 10.

Referring to another embodiment of an interface system depicted in FIGS. 10 and 11, an exemplary posterior strut 202 is preferably monolithic such that the posterior strut 202 is continuously formed and integrated with the transverse members 212, 213. As with the foregoing embodiments, the posterior strut 202 may generally form a T-shape, with the width $W_{HM}$ of the transverse members 212, 213 being less than the width $W_{VM}$ of the vertical member 210. According to this disclosure, the term "monolithic" should convey a unitary, one-piece construction, such as a die-cut piece of metal or injection molded plastic. The plastic can be reinforced with materials such as glass fibers, such as a glass-filled nylon.

By "monolithic," it can also be a combination of injection-molded plastic over a sufficiently stiff but malleable metallic core, comprising one or more metal frame members. The strut 202 may also be an injection molded part formed entirely of plastic having sufficient stiffness and strength to carry the prescribed loads of both transverse members 212, 213.

The vertical member 210 may be arranged in a substantially or completely flat configuration across the width $W_{VM}$. The vertical member 210 may have a curved cross-section across the width $W_{VM}$ to accommodate a user's spine, in contrast to a flat configuration. The transverse members 212, 213 may likewise have a substantially or completely flat configuration across the width $W_{HM}$.

An exemplary material is a 7075 aluminum alloy, however other structural materials are clearly envisioned including fiber-reinforced resins, metal alloys, and combinations thereof, sufficiently strong to support the shoulder assist mechanism, while offering a springy feel over the user's shoulders. The springy sensation softens the user's experience when wearing the shoulder support interface system with the shoulder assist mechanism. The springy feel results from resiliency of the posterior strut 202, and serves in part as a suspension for the shoulder assist mechanism.

Free ends 215, 217 of the transverse members 212, 213 may be arranged at an angle 220 out of plane from the vertical member 210. By definition of "out of plane," the free ends 215, 217 extend outwardly away from the vertical member 210 taken as if it is flat and lying in a plane, and the transverse members 212, 213 extending perpendicularly from the vertical member 110, particularly if viewed in a plan view.

Such angle 220 enables greater spring of the transverse members 212, 213 relative to the vertical member 210. The angle 220 may be modified and selected depending on an individual user, particularly by articulating the angle 220 from a transition line whereat each of the transverse members 212, 213 connects or continuously merges into the vertical member 210. The material forming the posterior strut 202 may be selected as being malleable in the sense that the angle of the transverse members 212, 213 can be selected and modified, but in use the transverse members 212, 213 do not lose the fixed angle 220 upon subjection of a load, and are sufficiently resilient to return to the angle 220 when the load is released.

The transverse members 212, 213 may also be arranged at an angle in the plane of bending of the vertical member 210, in that the transverse members 212, 213 are arranged in the plane of a hypothetically flat vertical member 210 and relative to a vertical axis A-A of the vertical member 210. The transverse members 212, 213 may be both arranged out of plane and angle within the plane of the vertical member 210. The transverse members 212, 213 may advantageously provide added resilience and comfort while also contouring to a user's dimensions more accurately, along the scapula and along thoracic and lumbar contours.

The vertical member 210 may define a plurality of relief openings 220 for providing relief over the user's spine, further creating a relatively lightweight and ventilated structure. The relief openings 220 are preferably arranged along the axis A-A.

The transverse members 212, 213 define elongate horizontal slots 226 generally perpendicular to the axis A-A to support the assistive device. Vertical slots 218 are at a lower section of the posterior strut 202 and are arranged for securing and adjusting the height of the base support, as discussed above. The horizontal slots 226 may be replaced by solid material, and in its place connection elements may be attached to the transverse members 212, 213 for connecting the assistive device. Vertical slots 218 and horizontal slots 226 allow the assistive device 117 to be positioned over a user's humeral head regardless of the user's particular dimensions, and facilitate a convenient and intuitive adjustment.

FIG. 11 shows how the vertical member 210 may be contoured relative to the axis A-A to customize the posterior strut 202 to an individual's spine. The vertical member 210 may have different zones of angularity 222, 224 along the length of the vertical member 210 relative to the axis A-A. Along the length A-A, preformed contours are located to conform to the user's anatomy at the thoracic contour (T) or at a lumbar contour (L). Vertical contouring at the intersection of the vertical and horizontal members creates proximate anatomical contouring to the scapulae. The resulting shape not only supports the back but it also provides a low profile contour of the strut overall. A minimal profile is preferable in a work or other environment to minimize the likelihood of inadvertently striking or catching on surrounding objects.

Figure 12:
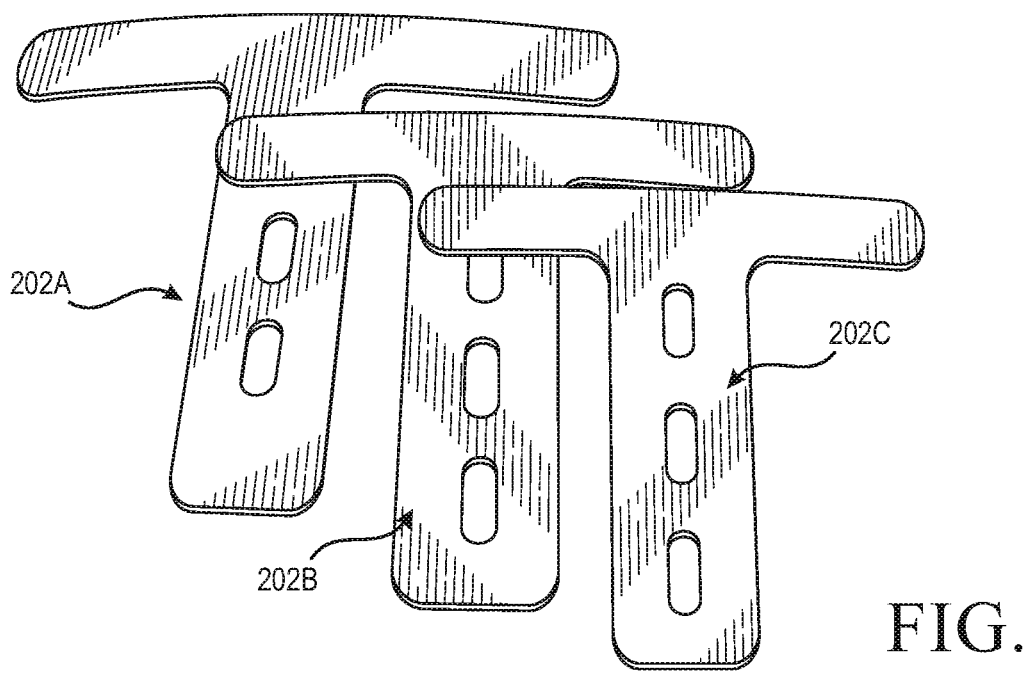
FIG. 12 is a schematic view showing a plurality of posterior struts having the configuration of FIG. 10 in different sizes.

FIG. 12 exemplifies how a plurality of differently sized posterior struts 202A, 202B, 202C may be available depending on sizes of the users, and may include different configurations of apertures for custom-selected fit, comfort, strength, resilience, weight, and etc.

Figure 13:
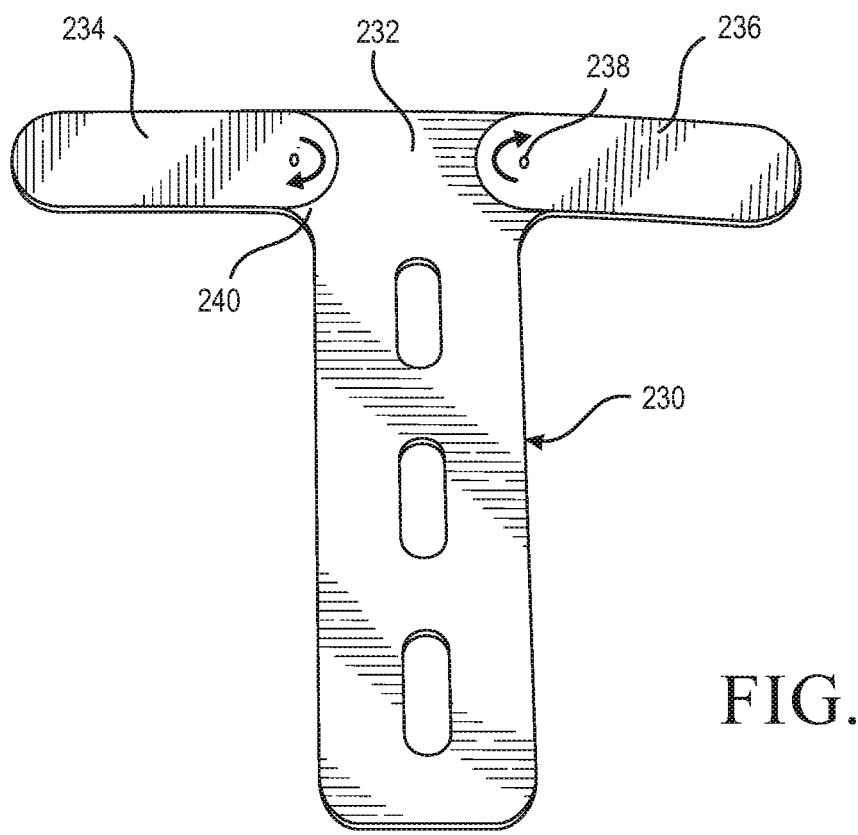
FIG. 13 is an elevational view of a variation of the posterior strut of FIG. 10 having articulating horizontal sections.

FIG. 13 depicts another embodiment of the posterior strut 230 including transverse members 234, 236 that articulate relative to the vertical member 232. Compared to the monolithic strut concept in aforementioned embodiments, which remains rigid in all three planes of motion, in this embodiment the transverse members 234, 236 pivot in the coronal plane. The transverse members 234, 236 pivot relative to the vertical member 232 at pivot points 238. The vertical member 232 may include underlying portions 240 that reinforce the transverse members 234, 236. In this embodiment, the posterior strut 230 is integrally formed from more than a monolithic one-piece construction, as in the embodiment of FIG. 6.

This pivoting articulation allows the strut to follow the normal anatomical rotational and sliding motion of the scapulae over the thorax during overhead reaching tasks and when scapular elevation or depression occur. While accommodating these relative coronal plane motions, the interface system continues to provide resistance to sagittal plane torques transmitted to the transverse members 234, 236 of the posterior strut 230 by the assistive elements. In this example, the ROM is relatively free in the coronal plane while transverse and sagittal plane motions are limited. Limits to end points of range of motion in this articulation may be preferred to limit motion to no farther than desired end points. By allowing or restricting ROM in various planes of motion, torques may be resisted by the posterior strut 230 in sagittal, coronal and transverse planes respectively while allowing movement in critical directions.

Figure 14:
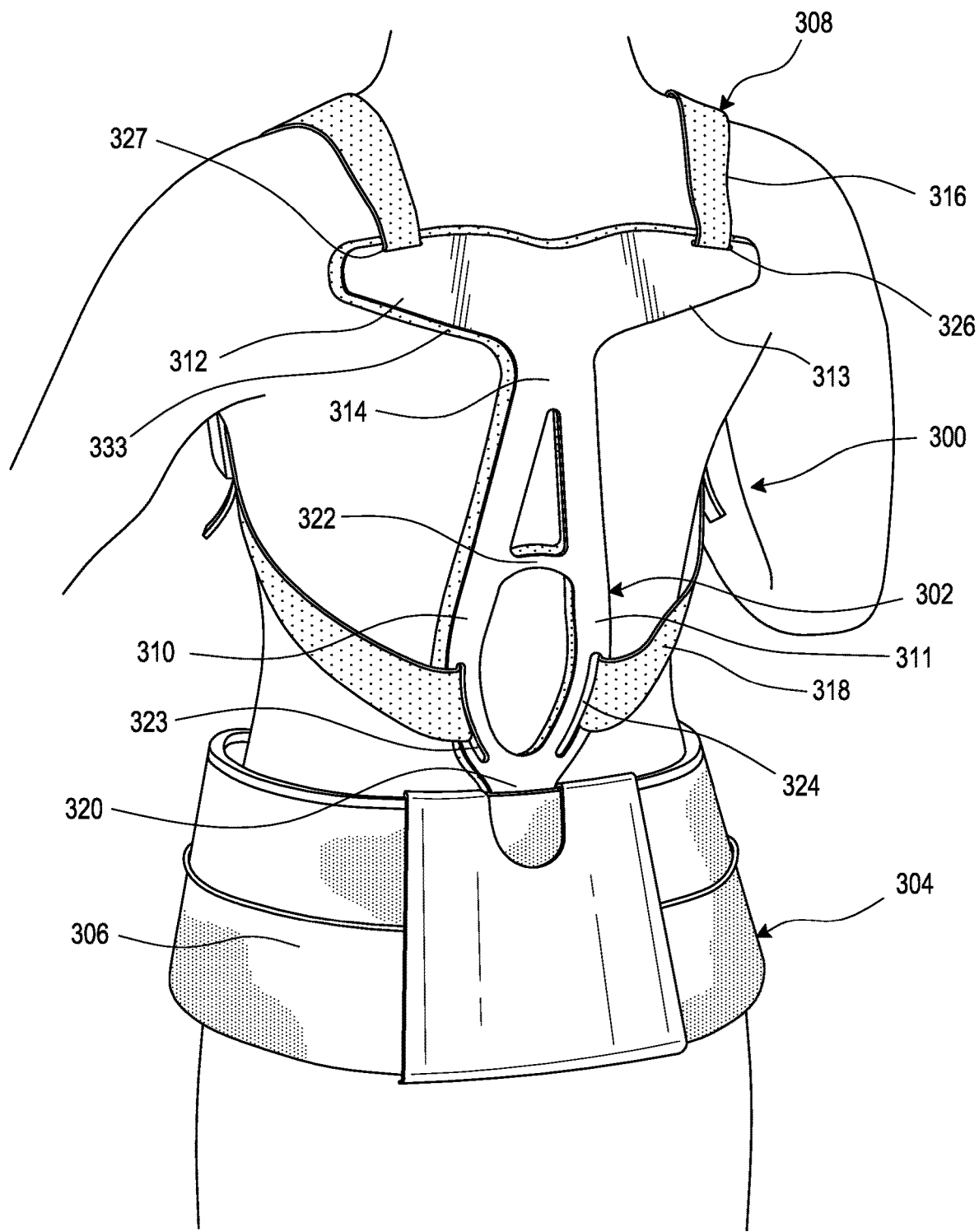
FIG. 14 is a rear perspective view of another embodiment of an interface system.

FIG. 14 illustrates another embodiment of an interface system 300 having a posterior strut 302 forming an ergonomic shape. The base support 304 connects to the posterior strut 302, and has belt segments 306, as in preceding embodiments. A shoulder strap assembly 308 likewise secures to the interface system 300, as in other embodiments, and may secure back to the posterior strut 302 from the transverse members 312, 313. At least the posterior strut 302 is lined with padding 333, and may be covered with fabric, coatings, or other materials. A posterior assembly 336 of the base support 304 is concealed by a covering.

Figure 16:
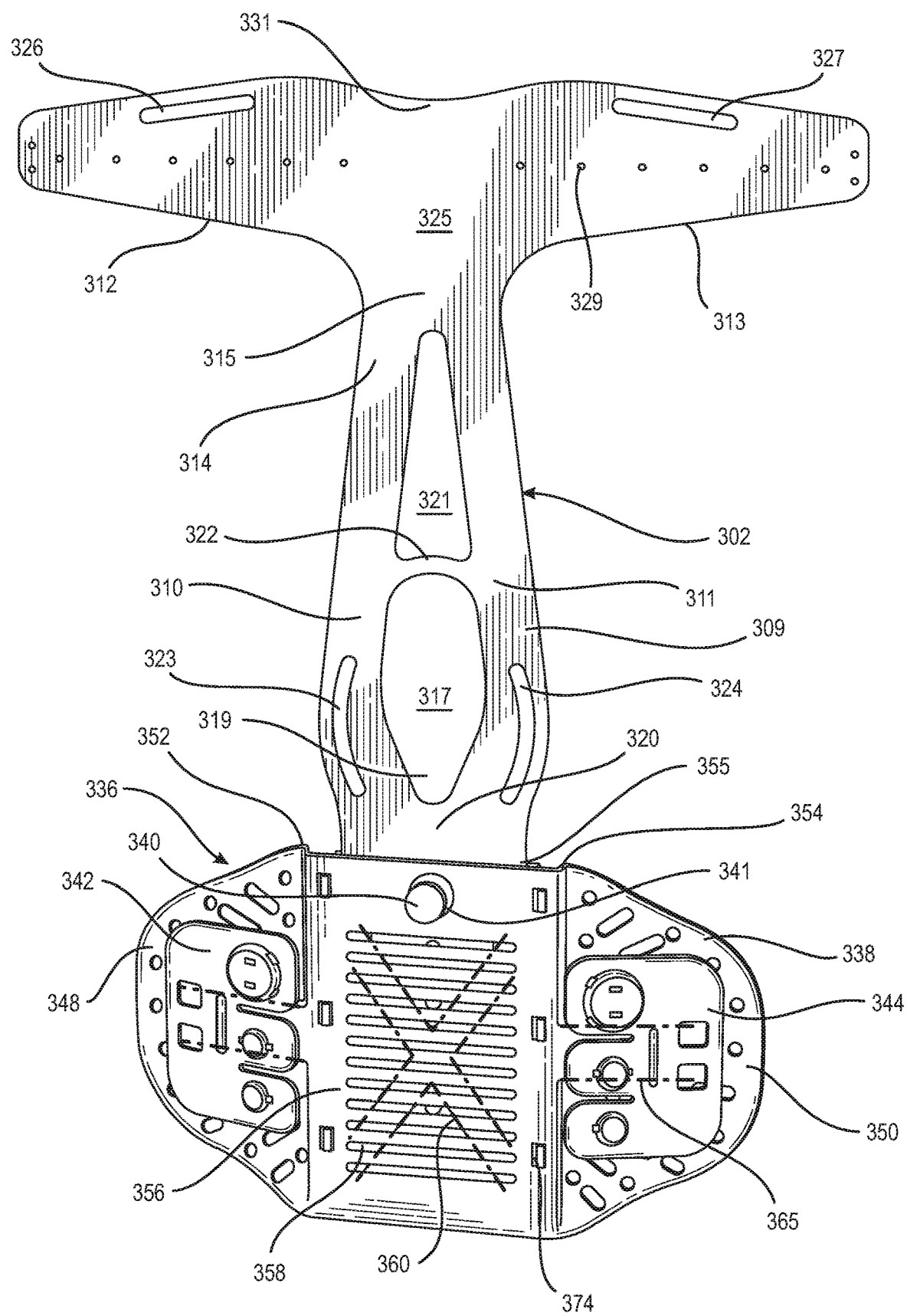
FIG. 16 is an exterior perspective view of a posterior assembly of the interface system in FIG. 14 stripped of coverings.
Figure 17:
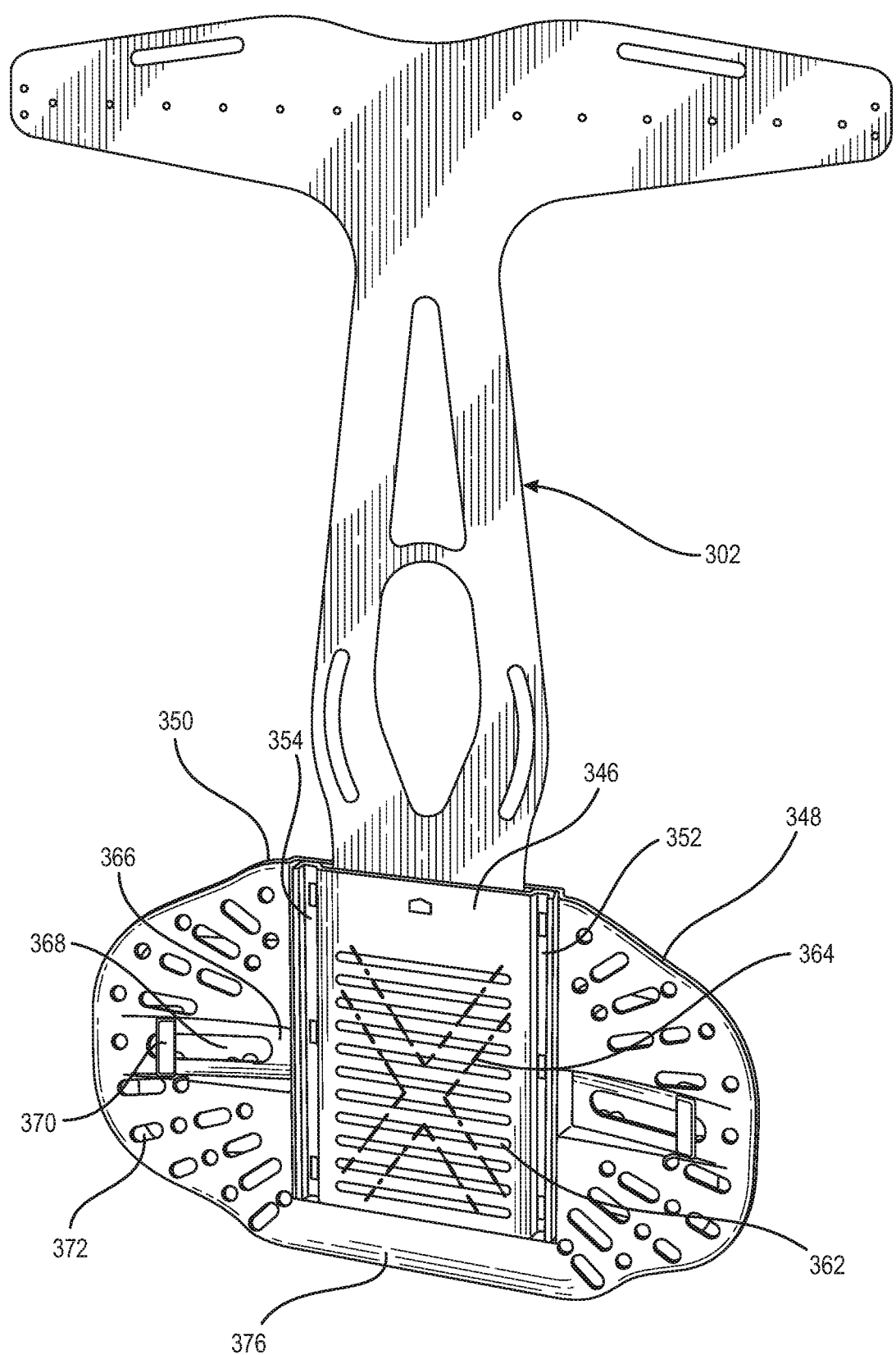
FIG. 17 is an interior perspective view of the posterior assembly of the interface system of FIG. 16.

FIGS. 14, 16, and 17 show a base portion 320 of the posterior strut 302 secured to the base support 304, as in any of the preceding embodiments. The posterior strut 302 has a lower portion 309 that bifurcates from the base portion 320 and has first and second segments 310, 311, that extend or flare from the base portion 320 to distribute pressure over the user's lower back. The base portion 320 may be wider than portions of the posterior strut 302 between an upper portion 314 whereat the first and second segments 310, 311 return together at a junction 315, particularly since the base portion 320 is secured to the base support 304.

In the depicted embodiment of FIG. 14, the lower portion 309 generally forms an oval shape with the base portion 320 and a bridge portion 322, and the first and second segments 310, 311. The lower portion 309 defines a first opening 317 and has a taper 319 as it approaches the base portion 320 to provide greater strength to the base portion 320, and to accommodate strap attachments 323, 324 about the lower portion 309 for receiving straps of the strap assembly 308. The lower portion 314 above the opening 317 may form a second opening 321 tapering toward the junction 315. Between the first and second openings 317, 321, the bridge portion 322 provides stability to the posterior strut 302, yet the first and second segments 310, 311 with the first and second openings 317, 321 avoid contact with the spinal column of the user, distributing compression over the paraspinal musculature of the user's back rather than the sensitive spinous processes at midline.

The large oval opening 317 also creates enhanced air circulation around the supporting strut near the lumbar and thoracic spine. The second strap attachments 323, 324 may follow an arcuate profile of the first and second segments 310, 311, particularly when they form an oval shape at the lower portion 309. The second strap attachments 323, 324 may be oversized relative to the second segments 318 of the strap assembly 308, in part to aid in varying the size or accommodating different sizes and contours of the users.

The first and second segments 310, 311 approach one another at the lower portion 314 and meet at the junction 315 below the transverse members 312, 313 and a transverse central portion 325. A central trough 331 may be above the transverse central portion 325 to provide better clearance below a user's neck, freeing up this region while offering rigidity below the central trough 331 at the transverse central portion 325.

The transverse members 312, 313 may possess crests on opposed sides of the central trough 331, and include first strap attachments 326, 327 so the first segments 316 of the strap assembly 308 secure on the posterior side of the interface system 300. The transverse members 312, 313 may taper at their free end portions opposite from the transverse central section 325, to minimize coverage over the user's shoulder blades. The second segments 318 may secure to the first and second segments 310, 311 along the lower portion 309 of the posterior strut 302.

The transverse members 312, 313, as in preceding embodiments, may define a plurality of openings 329 for selective and individualized attachment of assistive devices, as depicted in preceding embodiments. The plurality of openings 329 may generally be arrayed along the length of the transverse members 312, 313, although other arrangements may be provided according to the configuration of the assistive devices.

Referring to FIG. 15A, the anterior side of the interface system 300 may be adapted with an adjustable chest strap 332 having a buckle 334 for securing and adjusting the length of the chest strap 332. The chest strap 332 has an adjustment feature 328 permitting the chest strap 332 to slide up and down along sliders 330 on the first segment 316 of the strap assembly 308 to accommodate different user heights. As the chest strap 332 is tensioned and held by the buckle 334, the chest strap 332 is maintained relative to the first segment 316.

FIG. 15B exemplifies a variation of a chest strap 380. The chest strap 380 defines pad sections 383 along strap segments 384 of the straps 382 of the strap assembly (as shown in other embodiments). The strap segments 384 may be secured to the pad sections 383, with metal links 385 connecting the strap 382 below the pad sections 383. A buckle 388 connects two ends 386, 387 of the chest strap 380, which ends 386, 387 are slidably mounted along the strap segments 384 by slides 390. Fasteners 388, such as rivets, may reinforce the pad sections 383 in the strap assembly 380. Various positions 389 are provided along the segments which may serve as resting spots for the sliders 390.

FIG. 15C exemplifies an embodiment where the strap segments 384 comprise multiple discrete sections 394, 395, 396 that are non-contiguous, as the segments are contiguous in the embodiment of FIG. 15B. The junctions 397, 398 between the sections 394, 395, 396 serve as resting spots between each of the sections 394, 395, 396 for corresponding sliders, as in FIG. 15B.

FIGS. 16 and 17 illustrate the posterior assembly 336 of the interface system 300 stripped of coverings, and reveal the connection of the posterior strut 302 to the posterior assembly 336 of the base support 304. The posterior assembly 336 includes a main component 338 having first and second wings 348, 350 pivotally depending from a central part 356 along elongate pivot connections 352, 354. Pulley panels 342, 344 slidably secure on the wings 348, 350, and operate similarly as in the lumbar device disclosed in U.S. Pat. No. 8,172,779.

FIG. 17 particularly shows how the pulley panels 342, 344 may have sliders 370 that engage elongate, generally laterally-directed slots 368 formed by the wings 348, 350, as in U.S. Pat. No. 8,172,779. However, as it is preferred that the posterior assembly 336 remains substantially rigid at the central part 356 for securely holding the posterior strut 302, the wings 348, 350 may be provided with protruding ramps 365 on the exterior side, preferably rising toward the central part 356, and tapering toward the free ends of the wings 348, 350. The ramps 365 provide smooth operation of the pulley panels as they slide over the wings 348, 350 and transition over the elongate pivot connections 352, 354.

The shape of the ramps provides transitional rigidity from the central portion of the panel forming a substantially rigid sleeve 355, to the more flexible wings 348 and 350. The interior side of the wings 348, 350 have recesses 366 corresponding to the ramps 365 in which the sliders 370 are located so the sliders do not catch on any covering or portion thereof during operation or cause discomfort to the user. The elevation of the ramps 365 provides a smooth transition as the ramps 365 move over the wings 348, 350, and enables the loading to be spread or transitioned outwardly, and mitigates stress points over the wings 348, 350 to assure ease of tensioning of the base support 304.

According to tensioning of the base support 304, the wings 348, 350 are arranged to pivot about a user's waist, and can accommodate different waist sizes of users. The wings 348, 350 may be rigid or may exhibit flexibility to yield to a waist size of the user. Apertures 372 formed by the wings 348, 350 may offer ventilation and reduce weight of the device, and may be arranged individually or in a pattern to aid in flexure of the wings 348, 350 about the user's waist.

In the depicted embodiment of FIGS. 16 and 17, the apertures 372 are arrayed as spraying outwardly from the central part 356 in an anatomically accommodating manner to better yield to a shape or variety of shapes of users' waists. While the wings 348, 350 may yield to the user's waist, once the base support 304 is secured to a user, the wings 348, 350 serve as a firm foundation along with the central part 356 for rigidly securing the posterior strut 302 and assistive devices to the user during use.

A plate 346 secures to the central part 356 along an interior side thereof to form a rigid or substantially rigid sleeve 355 for receiving the base support 304 of the posterior strut 302. A locking part 340 secures to the central part 356, and may comprise a knob that is spring-biased in a hole 341 formed by the central part 356. The locking part 340 engages at least one of corresponding openings formed by the posterior strut 302 at the base portion 320 within the sleeve 355 to conveniently and intuitively regulate the height of the posterior strut 302 relative to the base support 304.

The plate 346 and the posterior assembly 336 together form a panel, as in FIG. 4. The panel forms the foundation for the belt members of the base support 304, as exemplified in FIG. 14, which creates a counterforce to the posterior strut 302, as shown in FIGS. 9A, 9B. The belt members stop the posterior strut from being pulled away distally or prying away from the body. As the weight of the arm pushes against the assistive device and is directed into the posterior strut 302, the base support 304 keeps the posterior strut 302 against the user's body dispersing and transferring forces thereon.

The sleeve 355 may be ventilated by openings 358, 362 on both the central part 356 and the plate 346. The central part 356 and the plate 346 may include reinforcing elements 360, 364 that provide rigidity to the sleeve 355 despite the openings 358, 362. The plate 346 may be removably secured to the central part 356 by connections 374. The inferior edge of the sleeve 355 is tapered 374 to minimize edge pressure felt by the user over the sacral area.

Figure 18A:
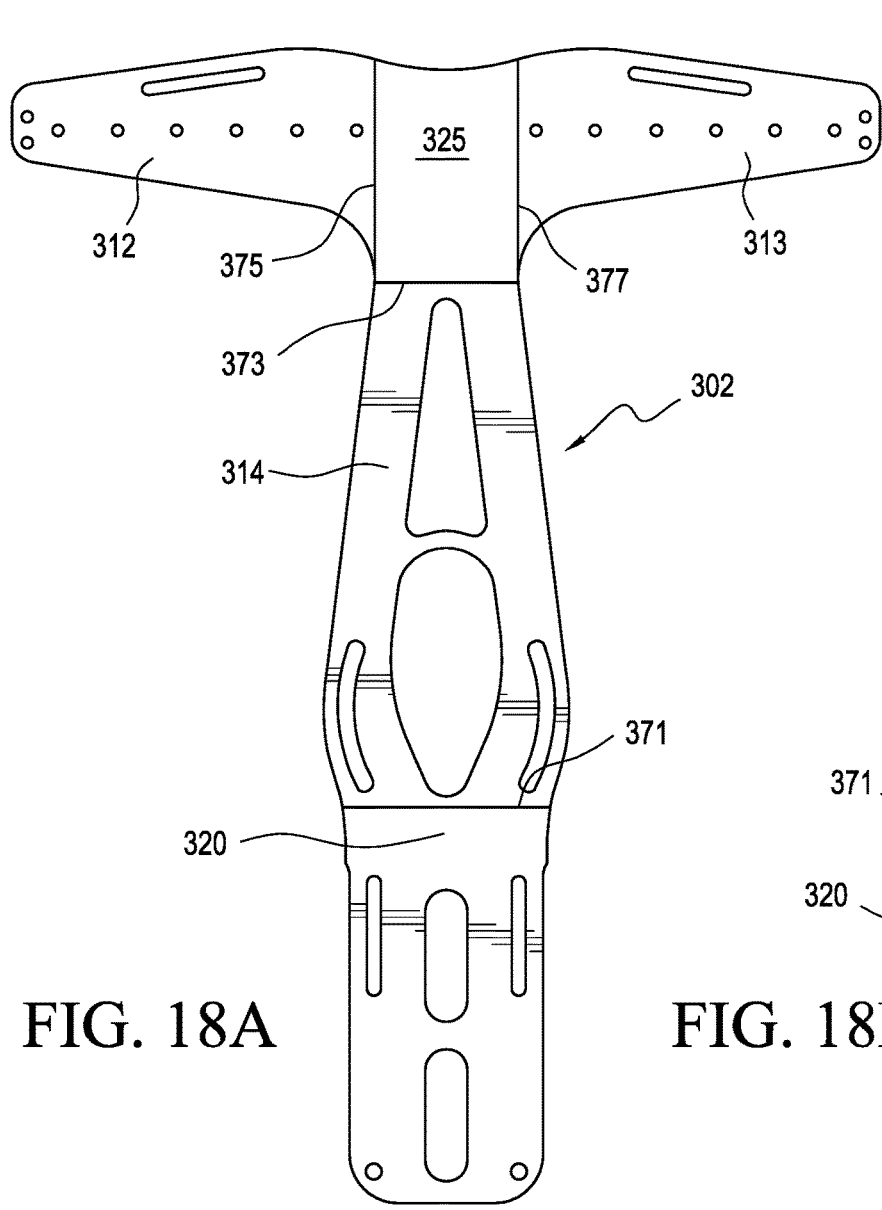
FIG. 18A is a front elevational view of the posterior strut in FIGS. 16 and 17.
Figure 18B:
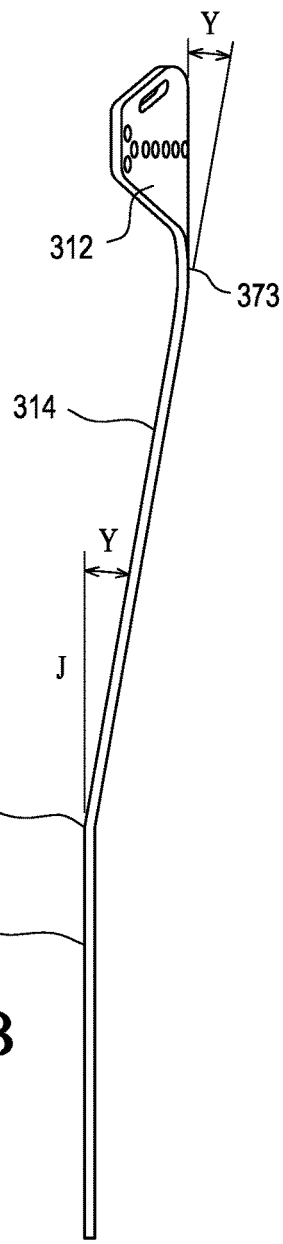
FIG. 18B is a side elevational view of the posterior strut in FIG. 18A.
Figure 18C:
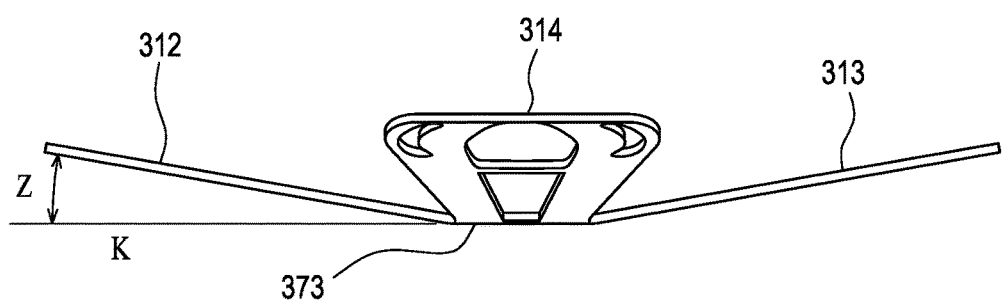
FIG. 18C is a partial plan view of the posterior strut in FIG. 18A with the base portion removed.

FIGS. 18A-18C exemplify the posterior strut 302, and how its various sections may be angled to better accommodate a user's anatomy or general user anatomies, particularly when originally in an anatomical position. The posterior strut 302 may be preconfigured to have angled relationships among the features to accommodate an anatomical position. While the posterior strut 302 may be rigid, it may likewise have springy or resilient properties to accommodate movement of the user and assistive devices or shocks thereto, while firmly stabilizing the assistive devices on the user's body.

The base portion 320 adjoins the upper portion 314 at border 371. The base portion 320, while remaining parallel along a vertical plane J, has a relationship with the upper portion 314 because the upper portion 314 extends outwardly relative to the vertical plane J at an exemplary angle of about 10 degrees. The upper portion 314 may extend substantially straight to a border 373 at the central portion 325, which may likewise extend parallel to the vertical plane J. The transverse members 312, 313 may extend inwardly from a horizontal plane K along which the central portion 325 lies, at an angle such as about 10 degrees defined at transition lines 375, 377. These angles are not limiting, and the posterior strut may be preconfigured in many angles suitable to individual users, when in the anatomical position, particularly when the posterior strut is malleable to position the portions of the posterior strut 302, yet sufficiently rigid in use to withstand permanently deforming from such positions in use.

By providing an interface system as described herein, the problems of exoskeleton devices being heavy, uncomfortable, and having poor alignment with a user's anatomy are overcome by the provision of an improved interface system with enhanced conformability to a user's dimensions and improved comfort. This is achieved by improved fit and location of the belt members, malleability of the vertical strut, and adjustment mechanisms that place an axis of rotation at the humeral head, improving comfort without sacrificing torque resistance.

It should be understood that not necessarily all objects or advantages may be achieved under any embodiment of the disclosure. Those skilled in the art will recognize that the embodiments may be embodied or carried out to achieve or optimize one advantage or group of advantages as taught without achieving other objects or advantages as taught or suggested.

Those skilled in the art will recognize the interchangeability of various disclosed features. Besides the variations described, other known equivalents for each feature can be mixed and matched by one of ordinary skill in this art to construct an interface system under principles of the present disclosure.

While the shoulder assist mechanism is briefly described, it is not limited to the depicted embodiments and the interface system may be adapted to accommodate different shoulder assist mechanisms.

The invention claimed is:

1. An interface system, comprising:
   a base support;
   a strap assembly; and
   a posterior strut having a vertical member defining a first end connecting to the base support, and a second end connecting to first and second transverse members extending in opposed directions from the vertical member, the first and second transverse members connecting to the strap assembly;

wherein the posterior strut has a length arranged to position the first and second transverse members from the vertical member at a spine of a scapula, and to create a concentric relationship between a humeral head and a rotational axis in a coronal plane, the vertical member is arranged in length distally to position the base support at or above an inferior costal margin of a user, wherein the vertical member has a widened configuration with a width arranged and positioned to transfer loads over a user's spine, and is wider than a width of the first and second transverse members;

wherein the first and second transverse members have ends arranged at an angle out of plane relative to the vertical member;

wherein an intermediate section of the posterior strut is arranged for deflection in sagittal and transverse planes.

2. The interface system of claim 1, wherein the posterior strut is monolithically formed and the vertical member continuously extends with the first and second transverse members.

3. The interface system of claim 2, wherein the posterior strut is formed from a single material uninterrupted between the vertical member and the first and second transverse members in a unitary construction.

4. The interface system of claim 1, wherein the first and second transverse members resiliently extend from the vertical member.

5. The interface system of claim 1, wherein the posterior strut is slidably adjustable in height relative to the base support.

6. The interface system of claim 5, wherein the base support includes a panel adjustably mounted to a lower section of the posterior strut.

7. The interface system of claim 1, wherein the first and second transverse members are arranged and positioned relative to the posterior strut to extend over a user's left and right scapula.

8. The interface system of claim 1, wherein the vertical member has a widened configuration at a lower section thereof relative to an intermediate section proximate to the first and second transverse members.

9. The interface system of claim 1, wherein the posterior strut defines an elongate vertical opening along an intermediate section of the posterior strut and is arranged to correspond to a spinal column.

10. The interface system of claim 9, wherein the posterior strut defines a lower opening in a lower section of the posterior strut located below the intermediate section, and has a shorter length than the elongate vertical opening.

11. An interface system, comprising:
a base support comprising a cinchable lumbar support;
a strap assembly; and
a posterior strut having a vertical member defining a first end connecting posteriorly to the base support, and a second end connecting to first and second transverse members extending in opposed directions from a central portion, the first and second transverse members connecting to the strap assembly, the posterior strut having a base portion secured to the base support, wherein the vertical member has a widened configuration with a width arranged and positioned to transfer loads over a user's spine, and is wider than a width of the first and second transverse members;
wherein the posterior strut has a lower portion located above and bifurcating from the base portion forming first and second segments separated by an opening, the first and second segments flare outwardly in a transverse direction from the base portion, the lower portion being wider than the base portion and an upper portion below the first and second transverse members and extending from the base portion, the first and second segments join at a junction at the upper portion below the central portion.

12. The interface system of claim 11, wherein a distal foundational support of the interface system is arranged to correspond at a level of a user's sacrum posteriorly and anterior superior iliac crest (ASIC) anteriorly, the posterior strut is arranged to resist torque applied to it at the first and second transverse members, the cinchable lumbar support extends from the base portion of the posterior strut and is arranged to extend around the anterior aspect of a user's body by forming a counter force to the torque placed on the posterior strut.

13. The interface system of claim 1, wherein the posterior strut is monolithically formed.

14. The interface system of claim 3, wherein the posterior strut is formed from a single material uninterrupted between the base portion and the first and second transverse members in a unitary construction.

15. The interface system of claim 1, wherein the base portion adjoins the lower portion at a border, the base portion is arranged parallel along a vertical plane of the posterior strut, the lower and upper portions extend outwardly relative to the vertical plane at an angle non-parallel to the vertical plane.

16. The interface system of claim 5, wherein the angle non-parallel to the vertical plane is at least greater than 0 degrees to about 10 degrees.

17. The interface system of claim 1, wherein the lower and upper portions extend substantially straight to the central portion, the central portion extending parallel to a vertical plane of the posterior strut, the first and second transverse members extend inwardly at an angle non-parallel relative to a horizontal plane along which the central portion lies.

18. An interface system, comprising:
a base support comprising a cinchable lumbar support;
a strap assembly; and
a posterior strut having a vertical member defining a first end connecting posteriorly to the base support, and a second end connecting to first and second transverse members extending in opposed directions from a central portion, the first and second transverse members connecting to the strap assembly, the posterior strut having a base portion secured to the base support;
wherein the posterior strut has a lower portion located above and bifurcating from the base portion forming first and second segments separated by an opening, the first and second segments flare outwardly in a transverse direction from the base portion, the lower portion being wider than the base portion and an upper portion below the first and second transverse members and extending from the base portion, the first and second segments join at a junction at the upper portion below the central portion;
wherein the base portion adjoins the lower portion at a border, the base portion is arranged parallel along a vertical plane of the posterior strut, the lower and upper portions extend outwardly relative to the vertical plane at an angle non-parallel to the vertical plane;
wherein the lower and upper portions extend substantially straight to the central portion, the central portion extending parallel to a vertical plane of the posterior strut, the first and second transverse members extend inwardly at an angle non-parallel relative to a horizontal plane along which the central portion lies.

\* \* \* \* \*